United States Patent
Diduch et al.

(10) Patent No.: US 10,751,161 B2
(45) Date of Patent: Aug. 25, 2020

(54) BICEPS TENODESIS ANCHOR IMPLANTS

(71) Applicant: DePuy Synthes Products, Inc., Raynham, MA (US)

(72) Inventors: David R. Diduch, Charlottesville, VA (US); Mark H. Getelman, Tarzana, CA (US); James J. Mahoney, Jr., Hyde Park, MA (US); Jacob A. Marks, Foxboro, MA (US); Gerome Miller, Randolph, MA (US); Matthew J. Ravenscroft, Mere (GB); Mehmet Z. Sengun, Canton, MA (US); Howard C. Tang, Boston, MA (US); Paul P. Weitzel, Newton, MA (US); Gregory R. Whittaker, Stoneham, MA (US)

(73) Assignee: MEDOS INTERNATIONAL SÁRL, Le Locle (CH)

( * ) Notice: Subject to any disclaimer, the term of this patent is extended or adjusted under 35 U.S.C. 154(b) by 0 days.

(21) Appl. No.: 14/610,626

(22) Filed: Jan. 30, 2015

(65) Prior Publication Data

US 2016/0113758 A1 Apr. 28, 2016

Related U.S. Application Data

(60) Provisional application No. 62/067,701, filed on Oct. 23, 2014.

(51) Int. Cl.
*A61F 2/08* (2006.01)

(52) U.S. Cl.
CPC .......... *A61F 2/0811* (2013.01); *A61F 2/0805* (2013.01); *A61F 2002/0835* (2013.01);
(Continued)

(58) Field of Classification Search
CPC ...... A61B 2017/0412; A61B 2017/042; A61B 2017/0422; A61B 2017/0424;
(Continued)

(56) References Cited

U.S. PATENT DOCUMENTS

| 651,949 A | 6/1900 | Lillie |
| 775,427 A | 11/1904 | Lusted |

(Continued)

FOREIGN PATENT DOCUMENTS

| AU | 2013201310 B2 | 5/2015 |
| CN | 1378439 A | 11/2002 |

(Continued)

OTHER PUBLICATIONS

European Search Report for EP Application No. 15191001.5, dated Apr. 1, 2016. (7 pages).
(Continued)

*Primary Examiner* — Christie L Bahena

(57) ABSTRACT

Various bone anchor assemblies and methods are provided for anchoring tissue to bone. In one embodiment, an anchor assembly for anchoring a tendon to bone is provided and includes a substantially cylindrical sheath having bone-engaging surface features formed on an external surface thereof, and having an inner lumen formed therein and extending from an open proximal end to a substantially closed distal. The substantially closed distal end includes at least one tendon anchoring feature extending distally therefrom and configured to facilitate anchoring of a tendon to bone. The anchor assembly further includes an expander having a generally elongate cylindrical configuration and being sized and shaped to be received within the inner lumen of the sheath.

11 Claims, 20 Drawing Sheets

(52) U.S. Cl.
CPC ............... *A61F 2002/0841* (2013.01); *A61F 2002/0858* (2013.01); *A61F 2002/0888* (2013.01)

(58) Field of Classification Search
CPC .... A61B 2017/0425; A61B 2017/0427; A61B 2017/0438; A61B 2017/044; A61B 2017/0445; A61B 2017/0464; A61B 17/0401; A61B 17/686; A61B 2017/0429; A61B 2017/043; A61B 2017/0432; A61B 2017/0433; A61B 2017/0435; A61B 2017/0437; A61B 2017/0446; A61B 2017/0448; A61B 2017/045; A61B 2017/0451; A61B 2017/0453; A61B 2017/0454; A61B 2017/0456; A61B 2017/0458; A61F 2220/0016; A61F 2/08; A61F 2/0805; A61F 2002/0817; A61F 2002/0823; A61F 2002/0829; A61F 2002/0835; A61F 2002/0841; A61F 2002/0858; A61F 2002/0864; A61F 2002/0888; A61F 2/0811; A61F 2002/0847; A61F 2002/0852; A61F 2002/087; A61F 2002/0876; A61F 2002/0882

See application file for complete search history.

(56) References Cited

U.S. PATENT DOCUMENTS

| | | | |
|---|---|---|---|
| 1,426,320 A | | 8/1922 | Reid |
| 1,925,385 A | | 9/1933 | Humes et al. |
| 2,243,717 A | | 5/1941 | Godoy |
| 2,288,584 A | | 6/1942 | Longfellow |
| 2,381,050 A | | 8/1945 | Hardinge |
| 2,484,655 A | | 10/1949 | Shreve |
| 3,073,189 A | | 1/1963 | Paige |
| 3,089,359 A | | 5/1963 | Poulin |
| 3,103,926 A | * | 9/1963 | Cochran ............... A61B 17/72 606/104 |
| 3,130,763 A | | 4/1964 | Bernard et al. |
| 3,298,410 A | | 1/1967 | Noboru |
| 4,503,737 A | | 3/1985 | DiGiovanni |
| 4,512,344 A | | 4/1985 | Barber |
| 4,592,346 A | | 6/1986 | Jurgutis |
| 4,640,271 A | | 2/1987 | Lower |
| 4,641,640 A | | 2/1987 | Griggs |
| 4,687,392 A | | 8/1987 | Bidwell |
| 4,704,055 A | | 11/1987 | Guhring |
| 4,711,232 A | | 12/1987 | Fischer et al. |
| 4,773,417 A | | 9/1988 | Moore et al. |
| 4,851,005 A | | 7/1989 | Hunt et al. |
| 4,858,810 A | | 8/1989 | Intlekofer et al. |
| 4,871,289 A | | 10/1989 | Choiniere |
| 4,901,717 A | | 2/1990 | Moore et al. |
| 4,919,130 A | | 4/1990 | Stoy et al. |
| 4,921,383 A | | 5/1990 | Fischer |
| 4,950,270 A | * | 8/1990 | Bowman ............ A61B 17/1714 606/304 |
| 4,960,420 A | | 10/1990 | Goble et al. |
| 4,976,715 A | | 12/1990 | Bays et al. |
| 4,988,351 A | | 1/1991 | Paulos et al. |
| 5,026,376 A | | 6/1991 | Greenberg |
| 5,029,573 A | | 7/1991 | Chow |
| 5,105,690 A | | 4/1992 | Lazzara et al. |
| 5,116,337 A | | 5/1992 | Johnson |
| 5,129,906 A | | 7/1992 | Ross et al. |
| 5,180,384 A | | 1/1993 | Mikhail |
| 5,209,756 A | | 5/1993 | Seedhom et al. |
| 5,211,647 A | | 5/1993 | Schmieding |
| 5,226,714 A | | 7/1993 | Wright |
| 5,226,890 A | | 7/1993 | Ianniruberto et al. |
| 5,234,435 A | | 8/1993 | Seagrave, Jr. |
| 5,236,445 A | * | 8/1993 | Hayhurst ............ A61B 17/0401 411/511 |
| 5,242,418 A | | 9/1993 | Weinstein |
| 5,258,012 A | | 11/1993 | Luscombe et al. |
| 5,266,075 A | | 11/1993 | Clark et al. |
| 5,273,024 A | | 12/1993 | Menon et al. |
| 5,290,296 A | | 3/1994 | Phillips |
| 5,290,297 A | | 3/1994 | Phillips |
| 5,314,427 A | | 5/1994 | Goble et al. |
| 5,320,626 A | | 6/1994 | Schmieding |
| 5,325,868 A | | 7/1994 | Kimmelstiel |
| 5,325,883 A | | 7/1994 | Orr |
| 5,352,229 A | | 10/1994 | Goble et al. |
| 5,352,231 A | | 10/1994 | Brumfield et al. |
| 5,380,334 A | | 1/1995 | Torrie et al. |
| 5,383,878 A | | 1/1995 | Roger et al. |
| 5,385,541 A | | 1/1995 | Kirsch et al. |
| 5,409,493 A | | 4/1995 | Greenberg |
| 5,425,490 A | | 6/1995 | Goble et al. |
| 5,425,733 A | * | 6/1995 | Schmieding ........ A61B 17/8645 606/104 |
| 5,445,642 A | | 8/1995 | McNulty et al. |
| 5,454,811 A | | 10/1995 | Huebner |
| 5,456,721 A | | 10/1995 | Legrand |
| 5,478,329 A | | 12/1995 | Ternamian |
| 5,505,735 A | | 4/1996 | Li |
| 5,527,341 A | | 6/1996 | Gogolewski et al. |
| 5,571,104 A | | 11/1996 | Li |
| 5,601,558 A | | 2/1997 | Torrie et al. |
| 5,601,562 A | | 2/1997 | Wolf et al. |
| 5,607,432 A | | 3/1997 | Fucci |
| 5,630,805 A | | 5/1997 | Ternamian |
| 5,632,748 A | | 5/1997 | Beck, Jr. et al. |
| 5,651,790 A | | 7/1997 | Resnick et al. |
| 5,653,763 A | | 8/1997 | Errico et al. |
| 5,655,330 A | | 8/1997 | Parsons, III |
| 5,658,289 A | | 8/1997 | Boucher et al. |
| 5,660,186 A | | 8/1997 | Bachir |
| 5,662,655 A | | 9/1997 | Laboureau et al. |
| 5,662,657 A | | 9/1997 | Carn |
| 5,669,925 A | | 9/1997 | Saunders |
| 5,676,499 A | | 10/1997 | Tukala |
| D388,171 S | | 12/1997 | Fekete |
| 5,700,266 A | | 12/1997 | Harryman, II |
| 5,702,398 A | | 12/1997 | Tarabishy |
| 5,713,903 A | | 2/1998 | Sander et al. |
| 5,720,753 A | | 2/1998 | Sander et al. |
| 5,738,666 A | | 4/1998 | Watson et al. |
| 5,746,743 A | | 5/1998 | Greenberg |
| 5,779,707 A | | 7/1998 | Bertholet et al. |
| 5,782,865 A | | 7/1998 | Grotz |
| RE36,020 E | | 12/1998 | Moore et al. |
| 5,895,351 A | | 4/1999 | Nottage et al. |
| 5,897,565 A | | 4/1999 | Foster |
| 5,899,906 A | | 5/1999 | Schenk |
| 5,899,938 A | | 5/1999 | Sklar et al. |
| 5,904,685 A | | 5/1999 | Walawalkar |
| 5,906,632 A | * | 5/1999 | Bolton ............... A61B 17/0401 606/232 |
| 5,941,882 A | | 8/1999 | Jammet et al. |
| 5,948,000 A | | 9/1999 | Larsen et al. |
| 5,948,001 A | | 9/1999 | Larsen |
| 5,957,953 A | * | 9/1999 | DiPoto ............... A61B 17/0401 606/232 |
| 5,961,520 A | | 10/1999 | Beck, Jr. et al. |
| 5,961,521 A | | 10/1999 | Roger |
| 5,968,078 A | | 10/1999 | Grotz |
| 5,993,458 A | | 11/1999 | Vaitekunas et al. |
| 6,024,758 A | * | 2/2000 | Thal ............... A61B 17/0401 606/232 |
| 6,027,523 A | | 2/2000 | Schmieding |
| 6,077,267 A | | 6/2000 | Huene |
| 6,117,139 A | | 9/2000 | Shino |
| 6,123,711 A | | 9/2000 | Winters |
| 6,143,016 A | | 11/2000 | Bleam et al. |
| 6,143,017 A | * | 11/2000 | Thal ............... A61B 17/0401 606/232 |
| 6,221,107 B1 | * | 4/2001 | Steiner ............... A61F 2/0811 623/13.13 |

(56) References Cited

U.S. PATENT DOCUMENTS

| | | | |
|---|---|---|---|
| 6,231,606 B1 | 5/2001 | Graf et al. |
| 6,251,119 B1 | 6/2001 | Addis |
| 6,270,518 B1 | 8/2001 | Pedlick et al. |
| D448,482 S | 9/2001 | Bellofatto et al. |
| 6,283,948 B1 | 9/2001 | McKernan et al. |
| 6,306,138 B1 | 10/2001 | Clark et al. |
| 6,319,270 B1 | 11/2001 | Grafton et al. |
| 6,325,805 B1 | 12/2001 | Ogilvie et al. |
| 6,379,361 B1 | 4/2002 | Beck, Jr. et al. |
| 6,405,863 B1 | 6/2002 | Dhindsa |
| 6,443,956 B1 | 9/2002 | Ray |
| 6,464,706 B1 | 10/2002 | Winters |
| 6,517,519 B1 | 2/2003 | Rosen et al. |
| 6,517,564 B1 | 2/2003 | Grafton et al. |
| 6,533,816 B2 | 3/2003 | Sklar |
| 6,544,281 B2 | 4/2003 | ElAttrache et al. |
| 6,554,862 B2 | 4/2003 | Hays et al. |
| 6,558,389 B2 | 5/2003 | Clark et al. |
| 6,562,044 B1 | 5/2003 | Cooper |
| 6,579,295 B1 | 6/2003 | Supinski |
| 6,592,587 B1 | 7/2003 | Roger |
| 6,599,290 B2 | 7/2003 | Bailey et al. |
| 6,613,065 B2 | 9/2003 | Lajtai |
| 6,632,245 B2 | 10/2003 | Kim |
| 6,663,605 B2 | 12/2003 | Chan |
| 6,673,115 B2 | 1/2004 | Resch et al. |
| 6,702,817 B2 | 3/2004 | Beger et al. |
| 6,712,822 B2 | 3/2004 | Re et al. |
| 6,755,815 B2 | 6/2004 | Schultz |
| 6,755,836 B1 | 6/2004 | Lewis |
| 6,780,188 B2 | 8/2004 | Clark et al. |
| 6,827,722 B1 | 12/2004 | Schoenefeld |
| 6,871,740 B1 | 3/2005 | Cao |
| 6,875,214 B2 | 4/2005 | Supinski |
| 6,875,216 B2 | 4/2005 | Wolf |
| 6,887,271 B2 | 5/2005 | Justin et al. |
| 6,939,379 B2 | 9/2005 | Sklar |
| 6,942,664 B1 | 9/2005 | Voor et al. |
| 6,955,678 B2 | 10/2005 | Gabriel et al. |
| 7,074,203 B1 | 7/2006 | Johanson et al. |
| 7,083,647 B1 | 8/2006 | Sklar et al. |
| 7,104,999 B2 | 9/2006 | Overaker |
| 7,204,839 B2 | 4/2007 | Dreyfuss et al. |
| 7,235,060 B2 | 6/2007 | Kraus |
| 7,261,716 B2 | 8/2007 | Strobel et al. |
| 7,309,346 B2 | 12/2007 | Martinek |
| 7,309,355 B2 | 12/2007 | Donnelly et al. |
| 7,329,272 B2 | 2/2008 | Burkhart et al. |
| 7,341,591 B2 | 3/2008 | Grinberg |
| 7,341,592 B1 | 3/2008 | Walters et al. |
| 7,413,542 B2 | 8/2008 | Kucklick et al. |
| 7,442,202 B2 | 10/2008 | Dreyfuss |
| 7,468,074 B2 | 12/2008 | Caborn et al. |
| 7,476,228 B2 | 1/2009 | Abdou |
| 7,481,830 B2 | 1/2009 | Wall et al. |
| 7,556,638 B2 | 7/2009 | Morgan et al. |
| 7,572,283 B1 | 8/2009 | Meridew |
| 7,588,575 B2 | 9/2009 | Colleran et al. |
| 7,611,521 B2 | 11/2009 | Lubbers et al. |
| 7,651,528 B2 | 1/2010 | Montgomery et al. |
| 7,697,861 B2 | 4/2010 | Shindo et al. |
| D615,572 S | 5/2010 | Harpaz |
| 7,713,300 B2 | 5/2010 | Meridew et al. |
| 7,736,364 B2 | 6/2010 | Stone |
| 7,766,920 B2 | 8/2010 | Ciccone et al. |
| 7,828,090 B2 | 11/2010 | Drivdahl et al. |
| 7,833,244 B2 | 11/2010 | Cerundolo |
| 7,837,731 B2 | 11/2010 | Sklar |
| 7,883,510 B2 | 2/2011 | Kim et al. |
| 7,909,826 B2 | 3/2011 | Serhan et al. |
| 7,918,288 B2 | 4/2011 | Drivdahl et al. |
| 7,922,730 B2 | 4/2011 | Raines, Jr. |
| 7,959,650 B2 | 6/2011 | Kaiser et al. |
| 7,963,952 B2 | 6/2011 | Wright, Jr. et al. |
| 7,963,983 B2 | 6/2011 | Cerundolo |
| 7,967,861 B2 | 6/2011 | Montgomery et al. |
| 7,993,369 B2 | 8/2011 | Dreyfuss |
| 8,012,083 B2 | 9/2011 | Kucklick et al. |
| 8,021,403 B2 | 9/2011 | Wall et al. |
| 8,034,083 B2 | 10/2011 | Abdelgany et al. |
| 8,043,308 B2 | 10/2011 | Bittenson |
| 8,048,158 B2 | 11/2011 | Hays et al. |
| 8,051,929 B2 | 11/2011 | Drivdahl et al. |
| 8,057,524 B2 | 11/2011 | Meridew |
| 8,075,575 B2 | 12/2011 | Gonzalez-Hernandez |
| 8,100,916 B2 | 1/2012 | Kumar et al. |
| 8,123,749 B2 | 2/2012 | Serhan et al. |
| 8,128,658 B2 | 3/2012 | Kaiser et al. |
| 8,187,309 B2 | 5/2012 | Castaneda et al. |
| 8,202,295 B2 | 6/2012 | Kaplan |
| 8,206,446 B1 | 6/2012 | Montgomery |
| 8,216,131 B2 | 7/2012 | Kucklick |
| 8,221,455 B2 | 7/2012 | Shurnas et al. |
| 8,221,498 B2 | 7/2012 | Boucher et al. |
| 8,226,714 B2 | 7/2012 | Beck, Jr. et al. |
| 8,231,654 B2 | 7/2012 | Kaiser et al. |
| 8,241,298 B2 | 8/2012 | Sengun et al. |
| 8,273,086 B2 | 9/2012 | Serhan et al. |
| 8,277,464 B2 | 10/2012 | Bittenson |
| 8,282,651 B2 | 10/2012 | Ciccone et al. |
| 8,292,555 B2 | 10/2012 | Shaffer |
| 8,328,716 B2 | 12/2012 | Schmieding et al. |
| 8,343,195 B2 | 1/2013 | Rathbun et al. |
| 8,348,972 B2 | 1/2013 | Soltz et al. |
| 8,361,152 B2 | 1/2013 | McCormack et al. |
| 8,377,089 B2 | 2/2013 | Lipchitz et al. |
| 8,430,909 B2 | 4/2013 | Dreyfuss |
| 8,435,293 B2 | 5/2013 | Donnelly et al. |
| 8,435,294 B2 | 5/2013 | Montgomery et al. |
| 8,465,545 B2 | 6/2013 | Montgomery et al. |
| 8,506,573 B2 | 8/2013 | Dreyfuss et al. |
| 8,512,376 B2 | 8/2013 | Thornes |
| 8,512,405 B2 | 8/2013 | Baird |
| 8,523,902 B2 | 9/2013 | Heaven et al. |
| 8,523,903 B2 | 9/2013 | Kilburn-Peterson et al. |
| 8,529,610 B2 | 9/2013 | Graf et al. |
| 8,535,377 B2 * | 9/2013 | Myers ................ A61B 17/0401 |
| | | | 623/13.14 |
| 8,545,535 B2 | 10/2013 | Hirotsuka et al. |
| 8,562,680 B2 | 10/2013 | Hays et al. |
| 8,608,765 B1 | 12/2013 | Jurbala |
| 8,617,197 B2 | 12/2013 | Friedman et al. |
| 8,617,219 B2 | 12/2013 | Oren et al. |
| 8,636,799 B2 | 1/2014 | Sklar et al. |
| 8,647,385 B2 | 2/2014 | Boucher et al. |
| 8,663,279 B2 | 3/2014 | Burkhart et al. |
| 8,663,325 B2 | 3/2014 | Graf et al. |
| 8,672,960 B2 | 3/2014 | Briganti et al. |
| 8,672,967 B2 | 3/2014 | DiMatteo et al. |
| 8,672,968 B2 | 3/2014 | Stone et al. |
| 8,721,650 B2 | 5/2014 | Fanton et al. |
| 8,747,470 B2 | 6/2014 | Beck, Jr. et al. |
| 8,758,227 B2 | 6/2014 | Kucklick et al. |
| 8,771,223 B2 | 7/2014 | Patton et al. |
| 8,771,303 B1 | 7/2014 | Jurbala |
| 8,778,023 B2 | 7/2014 | Sklar |
| 8,784,431 B1 | 7/2014 | Harder et al. |
| 8,790,368 B2 | 7/2014 | Sullivan et al. |
| 8,821,383 B2 | 9/2014 | Mirza et al. |
| 8,821,527 B2 | 9/2014 | Farnan et al. |
| 8,821,557 B2 | 9/2014 | Corradi et al. |
| 8,840,665 B2 | 9/2014 | Young et al. |
| 8,845,725 B2 | 9/2014 | Barwood et al. |
| 8,870,877 B2 | 10/2014 | Koogle, Jr. |
| 8,932,354 B2 | 1/2015 | Barwood et al. |
| 8,939,983 B2 | 1/2015 | Stone et al. |
| 8,956,410 B2 | 2/2015 | Donnelly et al. |
| 9,056,010 B2 | 6/2015 | Shea et al. |
| 9,060,748 B2 | 6/2015 | Housman et al. |
| 9,060,772 B2 | 6/2015 | Gonzalez-Hernandez |
| 9,095,331 B2 * | 8/2015 | Hernandez ......... A61B 17/0401 |
| 9,241,783 B2 * | 1/2016 | Trenhaile ............. A61F 2/0805 |
| 9,277,911 B2 * | 3/2016 | Hernandez ......... A61B 17/0401 |
| 9,289,283 B2 * | 3/2016 | Baird .................... A61F 2/0811 |

(56) References Cited

U.S. PATENT DOCUMENTS

| | | | |
|---|---|---|---|
| 9,301,751 B2* | 4/2016 | Sullivan | A61B 17/0401 |
| 9,314,240 B2 | 4/2016 | Paulk et al. | |
| 9,693,856 B2 | 7/2017 | Sengun et al. | |
| 9,795,412 B2 | 10/2017 | Sinha | |
| 9,833,229 B2* | 12/2017 | Hernandez | A61B 17/0401 |
| 2001/0021855 A1 | 9/2001 | Levinson | |
| 2002/0151977 A1 | 10/2002 | Paes et al. | |
| 2002/0164218 A1 | 11/2002 | Aguirre | |
| 2003/0125749 A1 | 7/2003 | Yuan et al. | |
| 2003/0153921 A1 | 8/2003 | Stewart et al. | |
| 2003/0153926 A1 | 8/2003 | Schmieding et al. | |
| 2003/0225456 A1 | 12/2003 | Ek | |
| 2003/0233095 A1 | 12/2003 | Urbanski et al. | |
| 2004/0068262 A1 | 4/2004 | Lemos et al. | |
| 2004/0073219 A1 | 4/2004 | Skiba et al. | |
| 2004/0073222 A1 | 4/2004 | Koseki | |
| 2004/0176767 A1 | 9/2004 | Bickley | |
| 2004/0193217 A1 | 9/2004 | Lubbers et al. | |
| 2004/0267361 A1* | 12/2004 | Donnelly | A61F 2/0811 |
| | | | 623/13.14 |
| 2005/0075668 A1 | 4/2005 | Lizardi | |
| 2005/0251137 A1 | 11/2005 | Ball | |
| 2006/0004378 A1 | 1/2006 | Raines et al. | |
| 2006/0015110 A1 | 1/2006 | Pepper | |
| 2006/0116685 A1 | 6/2006 | Urbanski et al. | |
| 2007/0005068 A1* | 1/2007 | Sklar | A61B 17/0401 |
| | | | 606/139 |
| 2007/0156153 A1* | 7/2007 | Jiang | A61F 2/0811 |
| | | | 623/13.14 |
| 2007/0162124 A1 | 7/2007 | Whittaker | |
| 2007/0255172 A1 | 11/2007 | Pflueger | |
| 2007/0288031 A1 | 12/2007 | Dreyfuss et al. | |
| 2008/0027430 A1 | 1/2008 | Montgomery et al. | |
| 2008/0109038 A1 | 5/2008 | Steiner et al. | |
| 2008/0161864 A1* | 7/2008 | Beck | A61F 2/0811 |
| | | | 606/326 |
| 2008/0215060 A1 | 9/2008 | Garcia et al. | |
| 2008/0228186 A1 | 9/2008 | Gall et al. | |
| 2008/0228224 A1 | 9/2008 | Sauer et al. | |
| 2008/0275431 A1* | 11/2008 | Stone | A61B 17/0401 |
| | | | 606/1 |
| 2008/0275469 A1 | 11/2008 | Fanton et al. | |
| 2009/0112270 A1 | 4/2009 | Lunn et al. | |
| 2009/0138043 A1 | 5/2009 | Kohm | |
| 2009/0171400 A1 | 7/2009 | van der Burg et al. | |
| 2009/0192608 A1 | 7/2009 | Paulos | |
| 2009/0275994 A1 | 11/2009 | Phan et al. | |
| 2009/0281581 A1* | 11/2009 | Berg | A61B 17/0401 |
| | | | 606/304 |
| 2009/0287259 A1 | 11/2009 | Trenhaile et al. | |
| 2009/0312782 A1 | 12/2009 | Park | |
| 2009/0318923 A1 | 12/2009 | Burkhart et al. | |
| 2010/0016869 A1 | 1/2010 | Paulk et al. | |
| 2010/0069958 A1 | 3/2010 | Sullivan et al. | |
| 2010/0106194 A1 | 4/2010 | Bonutti et al. | |
| 2010/0121348 A1 | 5/2010 | van der Burg et al. | |
| 2010/0145395 A1 | 6/2010 | Graf et al. | |
| 2010/0174369 A1* | 7/2010 | Wang | A61F 2/0811 |
| | | | 623/13.14 |
| 2010/0198271 A1 | 8/2010 | Leone | |
| 2010/0217393 A1 | 8/2010 | Theofilos | |
| 2010/0241124 A1 | 9/2010 | Housman et al. | |
| 2010/0249801 A1 | 9/2010 | Sengun et al. | |
| 2011/0004247 A1 | 1/2011 | Lechmann et al. | |
| 2011/0009885 A1 | 1/2011 | Graf et al. | |
| 2011/0015675 A1 | 1/2011 | Howard et al. | |
| 2011/0071579 A1* | 3/2011 | Reach, Jr. | A61B 17/0401 |
| | | | 606/327 |
| 2011/0098727 A1 | 4/2011 | Kaiser et al. | |
| 2011/0106013 A1 | 5/2011 | Whittaker et al. | |
| 2011/0106252 A1* | 5/2011 | Barwood | A61F 2/0811 |
| | | | 623/13.14 |
| 2011/0106253 A1 | 5/2011 | Barwood et al. | |
| 2011/0112550 A1 | 5/2011 | Heaven et al. | |
| 2011/0112558 A1 | 5/2011 | Whayne et al. | |
| 2011/0251621 A1 | 10/2011 | Sluss et al. | |
| 2011/0257691 A1 | 10/2011 | Sutterlin et al. | |
| 2011/0270323 A1 | 11/2011 | Olsen et al. | |
| 2012/0010668 A1 | 1/2012 | Shimko | |
| 2012/0057949 A1 | 3/2012 | Canizares, Jr. et al. | |
| 2012/0059379 A1 | 3/2012 | Homan et al. | |
| 2012/0109156 A1 | 5/2012 | Overes et al. | |
| 2012/0109299 A1 | 5/2012 | Li et al. | |
| 2012/0116459 A1 | 5/2012 | Nottmeier | |
| 2012/0130374 A1 | 5/2012 | Bouduban et al. | |
| 2012/0136357 A1 | 5/2012 | Torrie et al. | |
| 2012/0150190 A1 | 6/2012 | Rabiner et al. | |
| 2012/0150301 A1 | 6/2012 | Gamache et al. | |
| 2012/0211543 A1 | 8/2012 | Euteneuer | |
| 2012/0215232 A1 | 8/2012 | Olsen et al. | |
| 2012/0245686 A1 | 9/2012 | Park | |
| 2012/0316565 A1 | 12/2012 | Stark | |
| 2013/0006302 A1 | 1/2013 | Paulk et al. | |
| 2013/0103054 A1 | 4/2013 | Housman | |
| 2013/0103080 A1* | 4/2013 | Hernandez | A61B 17/0401 |
| | | | 606/232 |
| 2013/0125714 A1 | 5/2013 | Dahners | |
| 2013/0158597 A1* | 6/2013 | Hernandez | A61B 17/0401 |
| | | | 606/232 |
| 2013/0158664 A1 | 6/2013 | Palmatier et al. | |
| 2013/0190817 A1 | 7/2013 | Bouduban et al. | |
| 2013/0197534 A1 | 8/2013 | Lauderbaugh et al. | |
| 2013/0197591 A1 | 8/2013 | Corradi et al. | |
| 2013/0238036 A1 | 9/2013 | Sinha | |
| 2013/0267998 A1 | 10/2013 | Vijay et al. | |
| 2013/0268023 A1 | 10/2013 | Santangelo et al. | |
| 2013/0310842 A1 | 11/2013 | Winkler et al. | |
| 2013/0325128 A1 | 12/2013 | Perloff et al. | |
| 2013/0331942 A1 | 12/2013 | Baird | |
| 2013/0338710 A1 | 12/2013 | Heaven et al. | |
| 2014/0005686 A1 | 1/2014 | Patton et al. | |
| 2014/0046369 A1 | 2/2014 | Heaven et al. | |
| 2014/0081324 A1* | 3/2014 | Sengun | A61B 17/0401 |
| | | | 606/232 |
| 2014/0107713 A1 | 4/2014 | Pech et al. | |
| 2014/0171983 A1 | 6/2014 | Graf et al. | |
| 2014/0172095 A1 | 6/2014 | Graf et al. | |
| 2014/0188166 A1 | 7/2014 | Cobb et al. | |
| 2014/0228898 A1 | 8/2014 | Gordon | |
| 2014/0236183 A1 | 8/2014 | Graf et al. | |
| 2014/0243978 A1 | 8/2014 | Beck, Jr. et al. | |
| 2014/0243982 A1 | 8/2014 | Miller | |
| 2014/0249579 A1 | 9/2014 | Heaven et al. | |
| 2014/0257384 A1 | 9/2014 | Dreyfuss et al. | |
| 2014/0277133 A1 | 9/2014 | Foerster | |
| 2014/0277134 A1 | 9/2014 | ElAttrache et al. | |
| 2014/0309668 A1 | 10/2014 | Sullivan et al. | |
| 2014/0343604 A1 | 11/2014 | Frank | |
| 2014/0364862 A1 | 12/2014 | Bennett et al. | |
| 2015/0018878 A1 | 1/2015 | Rizk et al. | |
| 2015/0018947 A1 | 1/2015 | Barwood | |
| 2015/0039030 A1* | 2/2015 | Saliman | A61B 17/0401 |
| | | | 606/232 |
| 2015/0066042 A1 | 3/2015 | Cummins et al. | |
| 2015/0173741 A1 | 6/2015 | Housman et al. | |
| 2015/0190130 A1 | 7/2015 | Groh | |
| 2015/0238327 A1 | 8/2015 | Cheng et al. | |
| 2016/0113643 A1 | 4/2016 | Diduch et al. | |
| 2016/0113644 A1 | 4/2016 | Diduch et al. | |
| 2016/0113756 A1 | 4/2016 | Diduch et al. | |
| 2016/0113757 A1 | 4/2016 | Diduch et al. | |
| 2016/0113758 A1 | 4/2016 | Diduch et al. | |
| 2016/0310260 A1 | 10/2016 | Sengun et al. | |
| 2017/0265988 A1 | 9/2017 | Sengun et al. | |
| 2017/0290655 A1 | 10/2017 | Piccirillo et al. | |
| 2017/0290656 A1 | 10/2017 | Piccirillo et al. | |
| 2018/0296319 A1 | 10/2018 | Diduch et al. | |
| 2018/0344376 A1 | 12/2018 | Diduch et al. | |

(56) References Cited

U.S. PATENT DOCUMENTS

| | | | |
|---|---|---|---|
| 2019/0029805 A1 | 1/2019 | Piccirillo et al. | |
| 2019/0029806 A1 | 1/2019 | Piccirillo et al. | |

FOREIGN PATENT DOCUMENTS

| | | | | |
|---|---|---|---|---|
| CN | 101394795 | A | 3/2009 | |
| CN | 102098969 | A | 6/2011 | |
| CN | 102292032 | A | 12/2011 | |
| CN | 102438548 | A | 5/2012 | |
| CN | 102470007 | A | 5/2012 | |
| CN | 202515702 | U | 11/2012 | |
| CN | 102905629 | A | 1/2013 | |
| CN | 103209647 | A | 7/2013 | |
| CN | 103445850 | A | 12/2013 | |
| CN | 203789970 | U | 8/2014 | |
| DE | 10325139 | A1 * | 12/2004 | ........... A61B 17/686 |
| EP | 1110510 | A1 | 6/2001 | |
| EP | 3020371 | A2 | 5/2016 | |
| JP | 200513740 | A | 1/2005 | |
| JP | 2005-66135 | A | 3/2005 | |
| JP | 2005-506864 | A | 3/2005 | |
| JP | 2005-323700 | A | 11/2005 | |
| JP | 2007-50269 | A | 3/2007 | |
| JP | 2007-306979 | A | 11/2007 | |
| JP | 200886769 | A | 4/2008 | |
| JP | 2011516795 | A | 5/2011 | |
| JP | 2011-528270 | A | 11/2011 | |
| JP | 2014-171673 | A | 9/2014 | |
| WO | 9428799 | A1 | 12/1994 | |
| WO | 01/30253 | A1 | 5/2001 | |
| WO | 2007/110863 | A2 | 10/2007 | |
| WO | 2012129206 | A2 | 9/2012 | |
| WO | WO-2012125905 | A1 * | 9/2012 | ......... A61B 17/0401 |
| WO | 2012/129617 | A1 | 10/2012 | |
| WO | 2012138777 | A1 | 10/2012 | |
| WO | 2014150053 | A1 | 9/2014 | |

OTHER PUBLICATIONS

European Search Report for EP Application No. 15191002.3, dated Apr. 15, 2016. (8 pages).
European Search Report for EP Application No. 15191010.6, dated Apr. 4, 2016. (6 pages).
European Search Report for EP Application No. 15191011.4, dated Apr. 1, 2016. (6 pages).
European Search Report for EP Application No. 15191013.0, dated Apr. 14, 2016. (7 pages).
European Search Report for EP Application No. 16166686.2, dated Sep. 20, 2016. (8 pages).
European Search Report for EP Application No. 17165749.7, dated Aug. 21, 2017.
European Search Report for EP Application No. 17165700.0, dated Aug. 11, 2017. (12 pages).
Chinese Search Report issued in related CN Application No. 201510696822.2 (5 pages).
Translation of International Search Report for CN Application No. 201510697570.5 dated Mar. 1, 2019.
Translation of Chinese Search Report for CN Application No. 201510696510.1 dated May 26, 2019 (4 pages).
Chinese Search Report for CN Application No. 201510696528.1 dated Jun. 25, 2019 (16 pages).

* cited by examiner

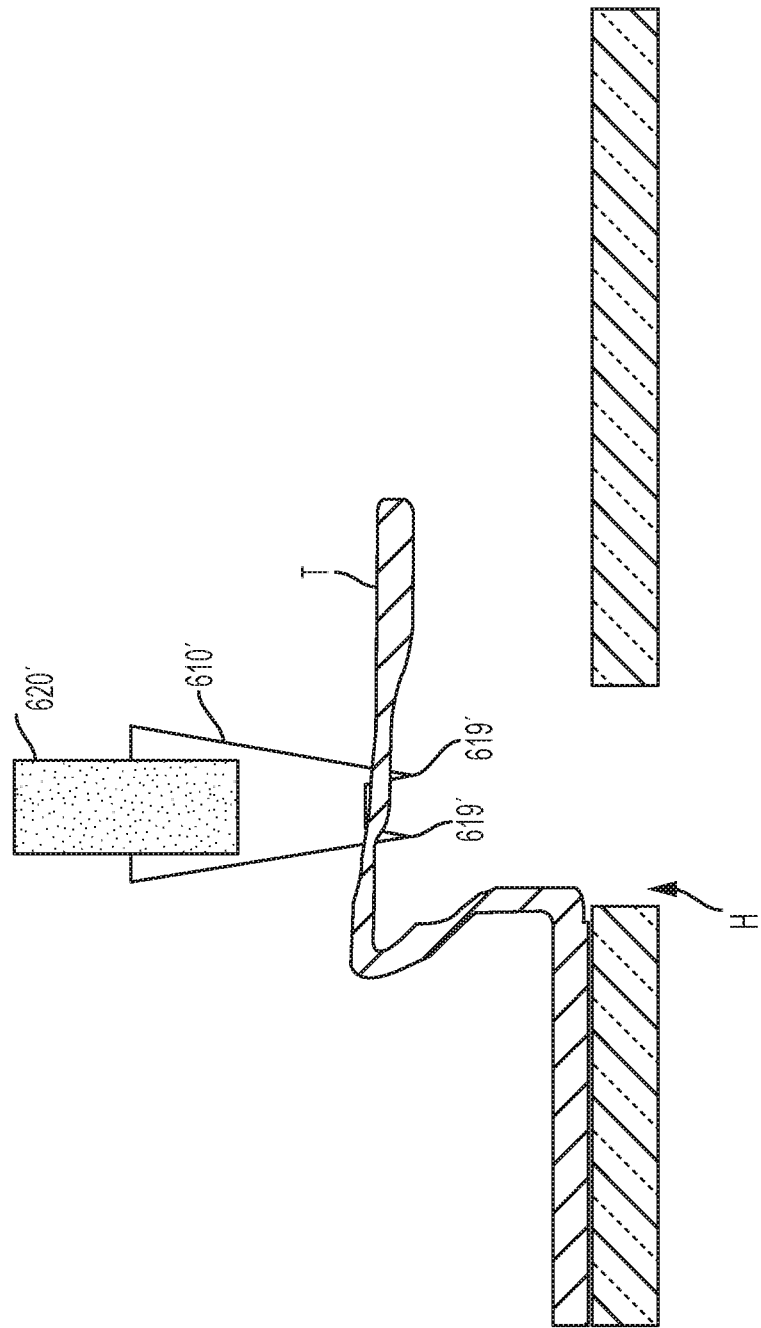

BICEPS TENODESIS ANCHOR IMPLANTS

CROSS REFERENCE TO RELATED APPLICATIONS

This application claims priority to U.S. Provisional Application No. 62/067,701 filed on Oct. 23, 2014 and entitled "Biceps Tenodesis Implants and Delivery Devices," which is hereby incorporated by reference in its entirety.

FIELD

Surgical devices and methods are provided for anchoring tissue to bone, and more particularly surgical implants and methods are provided for securing a biceps tendon to the humerus.

BACKGROUND

Disorders of the long head of the biceps tendon are a common source of shoulder pain and may occur in association with other diagnoses such as rotator cuff tears, superior labrum anterior posterior tears, impingement syndrome and capsular injuries, or may be present as an isolated source of shoulder pain. The treatment options for disorders of the long head of the biceps (LHB) continue to evolve and can include LHB tenodesis. In a tenodesis procedure, a suture is passed through the base of the LHB to locate the LHB in the subacromial space and to provide proximal control during the dissection. Once the suture is placed, the LHB is cut near the glenoid attachment. A sizer can be used to measure the tendon size and to thereby determine the appropriately sized bone screw. Once the screw is selected, a bone hole is drilled and a tendon fork is then used to push the tendon down into the bone hole. A bone screw is then delivered into the bone hole to anchor the tendon within the bone hole.

While current procedures can provide an effective means for anchoring a tendon to a bone, they can suffer several drawbacks. For example, current screws are rotated upon insertion into a bone hole. Such rotation of the screw relative to the tendon can lead to damage, tearing, severing, or misalignment of the tendon. This misalignment can change the desired tension and positioning of the tendon, leading to cramping, discomfort, and anatomical asymmetry. Moreover, it can be difficult to achieve a desired depth of the implant with respect to the bone hole.

Accordingly, there remains a need for improved tissue anchoring devices and methods, and in particular to anchors and methods for use in a biceps tenodesis procedure.

SUMMARY

Various bone anchor assemblies and methods are provided for anchoring tissue to bone. In one embodiment, an anchor assembly for anchoring a tendon to bone is provided and includes a substantially cylindrical sheath having bone-engaging surface features formed on an external surface thereof, and having an inner lumen formed therein and extending from an open proximal end to a substantially closed distal end. The substantially closed distal end includes at least one tendon anchoring feature extending distally therefrom and configured to facilitate anchoring of a tendon to bone. The anchor assembly further includes an expander having a generally elongate cylindrical configuration and being sized and shaped to be received within the inner lumen of the sheath. The expander can have a lumen extending at least partially therethrough for receiving a guidewire.

The tendon anchoring feature can have a variety of configurations. In one embodiment, the tendon anchoring feature can be at least one prong extending distally from a distal-facing surface of the sheath. For example, first and second prongs can extend distally from a distal-facing surface of the sheath and the prongs can extend substantially parallel to one another. In another embodiment, first, second, and third prongs can extend distally from a distal-facing surface of the sheath. The prong(s) can have a blunt or a pointed tip configuration. By way of non-limiting example, the prongs can be in the form of short or long spikes, cones, blunt posts, pointed or rounded cylindrical posts, barbed members, etc. In another embodiment, the at least one tendon anchoring feature can be in the form of first and second extension tabs extending distally from opposed sidewalls of the sheath. The tabs can define a generally U-shaped recess therebetween. In other aspects, the at least one tendon anchoring feature can be a semi-circular hook or a hoop having an opening formed therethrough for receiving a tendon.

The sheath can also have a variety of configurations. In one embodiment, the open proximal end of the sheath can include opposed flanges extending radially outward therefrom and configured to limit an insertion depth of the sheath into a bone hole. Alternatively, the open proximal end of the sheath can include at least one tab extending radially outward therefrom and configured to rest against a bone surface when the sheath is implanted in a bone hole. The sheath can include other features such as sidewalls channels or slots, internal threads, etc. The expander can also have a variety of configurations and in one embodiment the expander can be threaded for threadably mating with threads formed within the sheath. In other aspects, the sheath can include at least rib formed on the external surface thereof and extending longitudinally in a proximal-distal direction. The expander can also have various configurations. For example, the expander can include a flange extending radially outward from a proximal end thereof.

In another embodiment, an anchor assembly for anchoring a tendon to bone is provided and includes a sheath having a body with at least two sidewalls extending proximally therefrom. The sidewalls can define an inner lumen therebetween, and the sidewalls can have threads formed on an internal surface thereof. The sheath can further include a tendon engaging feature extending distally from a distal-most surface thereof. The tendon engaging feature can be configured to engage and retain a tendon within a bone hole. The anchor assembly can also include a threaded expander configured to be received between the pair of sidewalls and to threadably mate with the threads formed on the internal surface of the sidewalls. The sheath and the threaded expander can be configured such that, when the expander is fully threaded into the sheath, the sheath expands radially outward to retain a tendon within a bone hole due to compression.

As indicated above, the tendon engaging feature can have a variety of configurations, and can be in the form of at least two prongs spaced a distance apart from one another, folding prongs configured to move radially inward toward one another to engage a tendon therebetween, first and second extension tabs extending distally from opposed sidewalls of the sheath and defining a generally U-shaped recess therebetween, a hook-shaped member, a hoop having an opening therethrough for receiving a tendon, etc.

In other aspects, a method for anchoring a tendon to bone is provided and includes manipulating a sheath to engage a tendon with a tendon engaging feature extending distally from a distal end of the sheath, inserting the sheath, with the tendon coupled to the tendon engaging feature, into a bone hole such that the tendon extends around the sheath, and inserting an expander into the sheath to cause the sheath to expand radially outward to thereby anchor the tendon and the sheath within the bone hole. In one embodiment, the tendon engaging feature can be in the form of prongs that penetrate through the tendon to couple the tendon to the sheath. In another embodiment, the tendon engaging feature can be in the form of tabs whereby the tendon is positioned between the tabs. In another embodiment, the tendon engaging feature can be in the form of a hook that the tendon is hooked onto.

In another embodiment, a method for anchoring a tendon to a bone is provided and includes positioning a tendon across a bone hole and maintaining the tendon at a desired tension, positioning a sheath having a pair of tendon engaging features extending distally from the sheath proximate to the tendon, manipulating the sheath to determine an engagement point along the tendon at a distance from the bone hole, the distance being measured using the pair of tendon engaging features, and engaging the tendon at the engagement point with the pair of tendon engaging features and inserting the sheath with the tendon coupled thereto into the bone hole. In one embodiment, the distance can be substantially equal to a depth of the bone hole. In other aspects, the distance can be measured by rotating the sheath to move the prongs along the tendon.

BRIEF DESCRIPTION OF THE DRAWINGS

The invention will be more fully understood from the following description taken in conjunction with the accompanying drawings, in which:

FIG. 10E is a side view of the sheath and tendon of FIG. 10D, shown about to be inserted into the bone hole;

DETAILED DESCRIPTION

Figure 1:
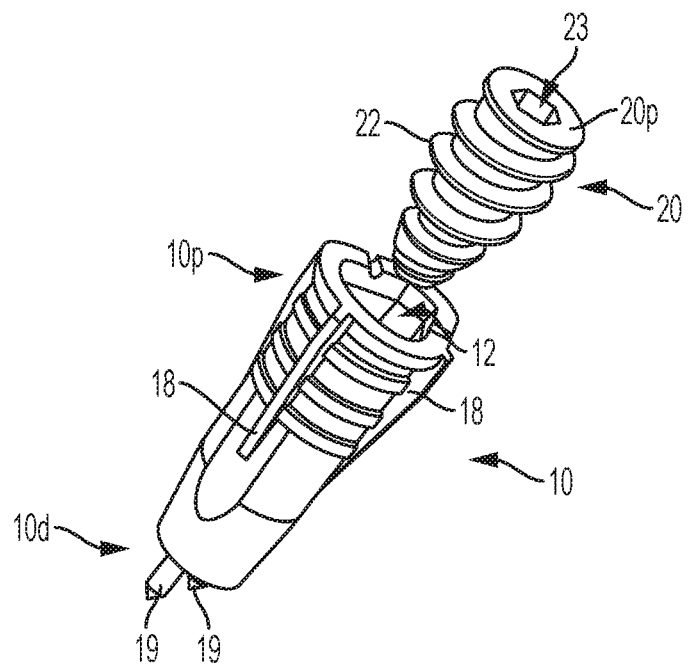
FIG. 1 is a perspective view of one embodiment of a biceps tenodesis anchor assembly having a sheath and an expander.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

In general, methods and devices are provided for anchoring tissue, such as a ligament or tendon, to bone. In an exemplary embodiment, the methods and devices are used to perform a biceps tenodesis surgery, however a person skilled in the art will appreciate that the devices and methods can be used in various procedures and for anchoring any tissue to bone. In one embodiment, a surgical implant is provided having a sheath and an expander that is received within the sheath. The sheath can include various tendon engaging features formed on a distal end thereof to help engage and insert the tendon into a bone hole. The sheath can also include various features on the proximal end thereof for compressing the tendon against the bone, facilitating introduction of the expander into the sheath, etc. The expander, when inserted into the sheath, can cause the sheath to expand radially outward, preferably at the cortical layer or beneath it, thereby anchoring the sheath and the tendon within the bone hole. A person skilled in the art will appreciate that the surgical implants and methods disclosed herein can be used with a variety of surgical devices, including inserter tools, driver tools, measuring devices, drills, and mallets, etc. Various exemplary tools are disclosed in U.S. patent application Ser. No. 14/610,600 entitled "Biceps Tenodesis Implants and Delivery Tools," and in U.S. patent application Ser. No. 14/610,730 entitled "Biceps Tenodesis Delivery Tools," each of which is filed on even date herewith and is incorporated by reference in its entirety.

In general, various anchor assemblies are provided that include a sheath and an expander. The sheath can have various configurations, but generally has an elongate substantially cylindrical shape with an inner lumen extending from an open proximal end to a closed distal end. While the distal end is described as being closed, it can include a blind bore formed on an internal surface thereof for receiving a guidewire, or it can include a bore extending fully therethrough for receiving a guidewire. The outer surface of the sheath can include one or more bone-engaging surface features formed along discrete portions thereof, or along an entire length thereof. The internal surface of the sheath can include features for mating with the expander, such as ribs or threads. As will be discussed in more detail below, the various sheath embodiments can also include a distal tendon engaging feature, such as one or more prongs, hooks, rings, tabs, etc., for poking, penetrating, grasping, or otherwise engaging a tendon to help push the tendon into a bone hole and/or to retain the tendon within the bone hole. The expander can also have a variety of configurations. For example, the expander can be in the form of a plug that can include one or more ribs that allow the expander to be press-fit or snap-fit into the sheath. Alternatively, the expander can be in the form of a threaded screw that threads into the sheath. The expander can also be a combination plug/screw where a distal portion is press/snap fit into the sheath and a proximal portion is threaded into the sheath. A person skilled in the art will appreciate that the sheath and the expander can each have a variety of configurations and that any one or more of the various features disclosed herein can be used in any combination to form a desired anchor assembly. Moreover, the various anchor assemblies disclosed herein can be formed from any bio-compatible materials, which can optionally be bio-absorbable. The sheath embodiments can each also be flexible or formed from a material that can deform radially outward when the expander is received therein. A person skilled in the art will appreciate that this can be achieved by varying the materials and/or wall thickness of the sheath.

The devices and methods described herein may have a number of advantages over existing techniques for preforming bicep tenodesis surgery. In particular, the entire attachment preparation procedure can be straightforward and requires a surgeon to take only a few quick steps to affix the implant structure including the sheath and the expander to bone. For example, the external tendon engagement features of the sheath can aid in inserting the tendon into the bone hole, maintaining the proper tension on the tendon, and anchoring the tendon properly. Additional tools for grasping and dunking the tendon into a bone hole are not required. A risk of damaging the tendon during insertion of the tendon into a bone hole is also reduced, as the sheath can be inserted into the bone hole without rotating the sheath. Since the expander is received within the sheath and does not directly contact the tendon, any rotation of the expander into the sheath will not cause any damage to the tendon. Accordingly, a risk of causing trauma to the tendon can be reduced and a time required to prepare and affix the tendon can be significantly reduced, which can facilitate the surgery and mitigate inconvenience to the patient. In addition, the described techniques can help to save operating room costs.

Figure 2:
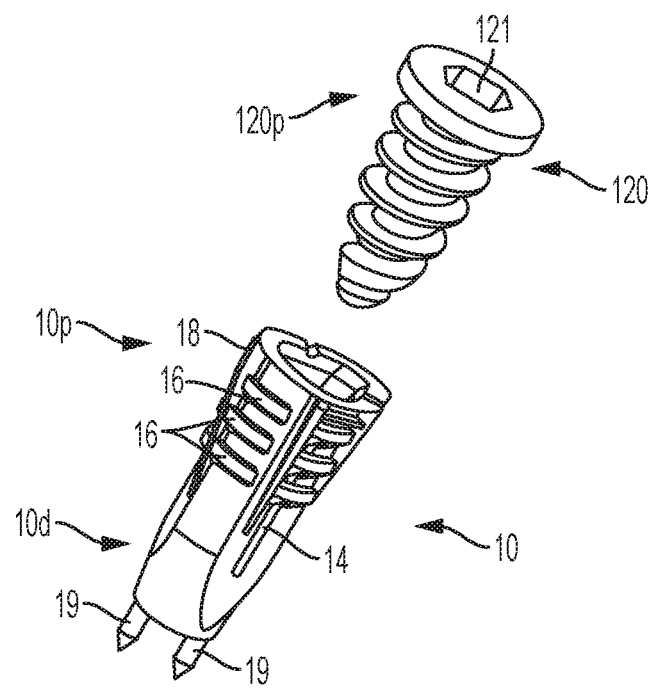
FIG. 2 is a side perspective view of the sheath of FIG. 1 and another embodiment of an expander.
Figure 3:
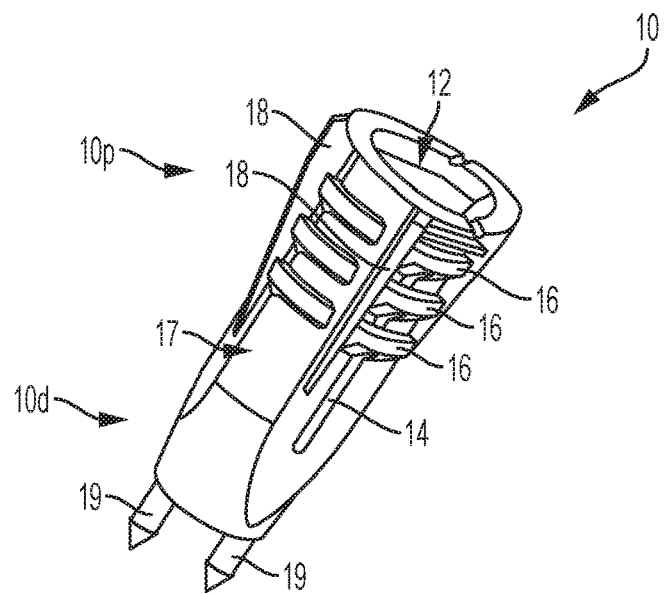
FIG. 3 is a perspective view of the sheath of FIG. 1.

FIGS. 1-3 illustrate one embodiment of a biceps tenodesis implant or anchor assembly that includes a sheath 10 and an expander, which is in the form of a screw 20. In general, the sheath 10 is configured to seat a tendon therearound, and to receive the expander screw 20 therein which is effective to cause the sheath 10 expand into bone to anchor the tendon within a bone hole.

The sheath 10 can have a variety of shapes and configurations. As shown, the sheath 10 has an elongate cylindrical shape with an open proximal end 10p having a proximal facing surface, and a closed distal end 10d having a distal facing surface. The sheath 10 includes an inner lumen 12 extending from the open proximal end 10p and terminating just proximal to the closed distal end 10d. As further shown, the sheath 10 has a substantially triangular cross-sectional geometry that generally defines three sidewalls, as will be described below with respect to FIG. 5. The cross-sectional shape can, however, vary and can be square, circular, ovular, etc. The cross-sectional shape can also vary along the length thereof. The inner surface of the sheath 10 can include various features to facilitate mating with an expander, such as screw 20. While not shown, the inner lumen can include threads or ribs formed therein for engaging the screw 20. The outer diameter of the sheath 10 can also vary, but in an exemplary embodiment the outer diameter is substantially constant along a proximal portion of the sheath, and it tapers distally inward along a distal portion of the sheath, as shown. The proximal and distal facing surfaces of the sheath 10 can also vary. In some embodiments, the proximal surface can be convex to match the contour of the bone, and the distal surface can be concave or saddled to seat the tendon thereon.

As indicated above, the sheath 10 is configured to receive the expander screw 20 therein, and to expand to be anchored within a bone hole. In order to facilitate expansion, the sheath 10 can include one or more relief channels 14 extending longitudinally along the sheath 10 and configured to break apart to allow radial expansion of the sheath. In the illustrate embodiment, the sheath 10 includes two relief channels 14 (only one channel is shown) formed in opposed sidewalls thereof such that the sheath 10 can split in half. While the position of the channels 14 around the circumference of the sheath can vary, in an exemplary embodiment the channels are arranged so as to allow the sheath to separate and expand in the direction that the tendon extends, as will be discussed in more detail below with respect to FIG. 5. In the illustrated embodiment, the relief channels 14 are positioned at a substantial mid-point of two of the three sides of the triangular cross-sectional shape. The relief channels 14 extend from the proximal end 10p and terminate just proximal to the closed distal end 10d, as best shown in FIG. 3 (only one relief channel is shown). The relief channels can be formed on the inner, outer, or both surfaces of the elongate body and can be in the form of a channel or groove that results in a thinned wall section of the sheath. In other embodiments, the relief channel can extend entirely through the sheath in certain regions, with the sidewalls being attached in only discrete locations.

As further shown in FIGS. 1-3, the sheath 10 can also include bone-engaging surface features formed on an external surface thereof. In the illustrated embodiment, the sheath includes a plurality of ribs 16 extending radially therearound and spaced longitudinally along a proximal portion thereof. The distal portion of the sheath is free of surface features. The illustrated ribs are uni-planar and do not form threads, as the sheath 10 is preferably not rotated during insertion into a bone hole. While only three ribs 16 are shown, the sheath can include any number of ribs. Each rib can have various cross-sectional geometries, including square, triangular, etc. The ribs can also have a particular directional orientation to help engage the tendon. The sheath can also include one or more longitudinal ribs 18 extending in a proximal-distal direction. These ribs can define a recess 17 therebetween for seating the tendon, thereby allowing the tendon to wrap around the sheath 10. The position of the longitudinal ribs 18 can vary, but in an exemplary embodiment the ribs are formed at a location that positions the tendon in the desired orientation when seated in a bone hole, as will be discussed in detail below with respect to FIG. 5. The radial ribs 16 can extend between the longitudinal ribs 18 such that the tendon will overly the radial ribs 16.

As further shown in FIGS. 1-3, the sheath 10 can include one or more distal tendon engaging features to engage and or manipulate a tendon during the insertion technique and/or to maintain the position of the tendon after insertion of the anchor implant. Furthermore, the distal features can continue to engage the tendon after the tendon is anchored within the bone hole. The features can have various configurations, such as external ribs, a single distal tip, or a plurality of distal tips, a circular or semi-circular hook, fin guides, expansion tips, anchoring tips, tendon graspers, etc. In this embodiment, the tendon engaging feature is in the form of first and second prongs 19 that extend distally from the distal facing surface of the sheath 10. Each prong can have a generally elongate configuration with a blunt tip for poking a tendon without penetrating the tendon, or with a pointed tip as shown for penetrating into a tendon. The tip can also include a head formed thereon to prevent pull-out of the prong from the tendon. The prongs 19 can extend at various angles relative to one another, including substantially parallel to one another as shown. The prongs are preferably positioned a distance apart from one another. The distance can vary depending on the desired use. In the illustrated embodiment, the prongs 19 are positioned inward of the outer perimeter at the distal end 10d of the sheath 10, however the prongs 19 are on opposite sides of the distal end of the sheath 10. As a result, the prongs 19 will be spaced a distance apart that is less than a width of a tendon to be anchored such that the prongs 19 can penetrate into the tendon to engage and manipulate the tendon. In other embodiments, as will be discussed in more detail below, the prongs can extend from the outer sidewalls of the sheath so as to allow a tendon to be received therebetween. The position of the prongs with respect to the tendon will be discussed in more detail below with respect to FIG. 5.

As indicated above, the sheath 10 is configured to receive an expander, e.g., screw 20. In the embodiment of FIG. 1, the expander screw 20 has a generally elongate cylindrical configuration with a constant minor diameter along at least a proximal portion, and preferably along a majority of the length, e.g., more than half of the total length. In other embodiments, however, the screw can be tapered along an entire length or portions thereof, or can be bullet shaped. A distal portion of the expander can taper distally inward to a reduced diameter at the distal-most end. The expander can have threads formed there along and extending along the entire length to facilitate engagement with the sheath upon insertion. In some embodiments the threads can extent partially along the body of the expander. The height of the threads 22 can vary, for example, the height can decrease toward the distal end to form a tapered distal tip. Such a configuration can facilitate insertion of the expander screw 20 into the sheath 10. When inserted fully therein, the proximal end 20*p* of the expander can sit flush with the proximal end 10*p* of the sheath 10. Alternatively, the expander can sit slightly proud or slightly recessed, as may be desired. In another embodiment, shown in FIG. 2, the expander screw 120 can include a head 121 formed on the proximal end 120*p* thereof. The head can have an enlarged diameter as compared to the remainder of the screw. The diameter can also be greater than a maximum diameter of the proximal end 10*p* of the sheath 10. Such a configuration will allow the head to rest against the proximal end of the sheath 10, and to compress the tendon between the head 121 and the bone surface. Each expander screw can also be fully cannulated for allowing the screw to be delivered over a guidewire. The screws can further have a flat proximal facing surface and a flat distal facing surface, or in other embodiments the proximal and distal surface shapes can vary. For example, the proximal surface can be convex to conform to the bone surface.

In use, the implant screws 400, 420 are configured to be inserted into the sheath 100 to cause the sheath 100 to expand. In an exemplary embodiment, the threads Ht have a height that is less than a height of the thread grooves 426 formed in the sheath, thus allowing the minor diameter $D_1$ of the screw 420 to contact the major diameter of the sheath 100 and thereby cause expansion of the sheath 100. As a result, the threads are not sized to cause expansion of the sheath 100, and rather than minor diameter of the screw 400, 420 causes expansion. Additionally, the implant screw can be shaped to cause the thicker mid-portion of the sheath to expand radially outward by a distance that is greater than the proximal and distal ends of the sheath, such that the mid-portion forms the largest diameter of the sheath in the expanded state, as previously discussed with respect FIG. 2.

A person skilled in the art will appreciate that the sheath 10 and expander screw 20, 120 of FIGS. 1-3, as well as the remaining sheath and expander embodiments disclosed herein, can include various other features to facilitate implantation into a bone hole. With reference to FIG. 1 by way of non-limiting example, the expander screw 20 can include a drive socket, e.g., a hex socket 23, formed in the proximal end 20*p* thereof and configured to receive a drive feature, e.g., a hex feature, on a driver tool. The sheath 10 can similarly include features to facilitate insertion into a bone hole, such as a threaded bore formed in the inner surface of the solid distal end for mating to a threaded tip of a guidewire, or any other drive feature formed therein for mating to a driver tool.

Figure 4:
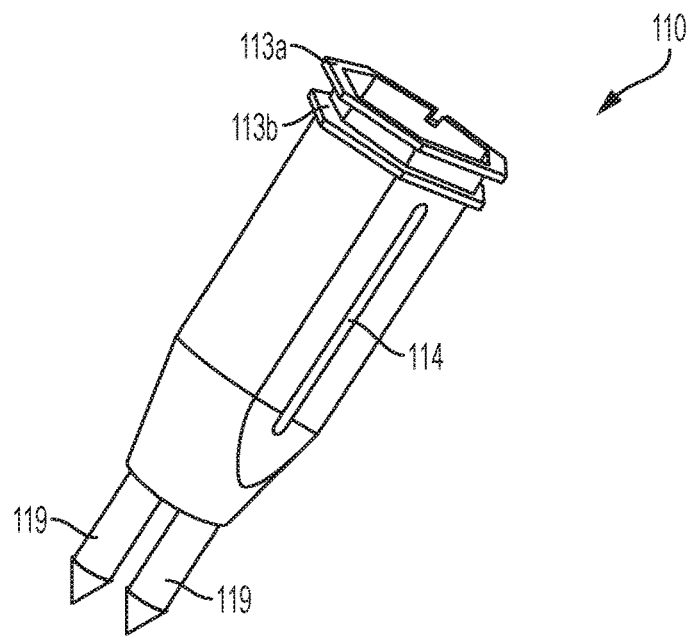
FIG. 4 is a side perspective view of another embodiment of a sheath.

FIG. 4 illustrates another embodiment of a sheath 110 that is similar to the sheath 10 in FIGS. 1-3 in that it has a generally triangular cross-sectional shape with three sidewalls along at least a proximal portion thereof. Other cross-sectional regions can be circular, or a combination of circular and triangular. In this embodiment, the sheath 110 does not have any longitudinal or radial ribs formed thereon, however such features can be included. The sheath 110 does, however, include an anti-plunge flange 113*a* formed thereon, and a cortical retaining flange 113*b* formed thereon. The anti-plunge flange 113*a* extends radially outward from the proximal-most end of the sheath 110 and can have a diameter that is greater than a diameter of a bone hole so as to act as a hard stop to limit an insertion depth of the sheath into the bone hole. The anti-plunge flange 113*a* can also function to compress a tendon against the bone surface to help prevent slippage of the tendon. The cortical retaining flange 113*b* is positioned a distance apart from the anti-plunge flange, and it can be configured to expand underneath the cortical bone surface when the sheath is implanted so as to prevent pull-out of the sheath. In particular, the cortical retaining flange 113*b* and the anti-plunge flange 113*a* can be spaced apart so as to allow the entire thickness, e.g., 1-2 mm, of cortical bone to be received therebetween. In other words, when the sheath is implanted and the anti-plunge flange 113*a* is resting on a bone surface, the cortical retaining flange 113*b* can extend underneath the cortical bone. The cortical retaining flange 113*b* can have a diameter that is less than a diameter of the anti-plunge flange 113*a* such that the cortical retaining flange 113*b* can pass into the bone hole. When the sheath 110 is expanded by the expander screw, the cortical retaining flange 113*b* can expand radially beyond the opening in the cortical bone, thereby sitting underneath the bone to prevent pull-out of the sheath.

Figure 5:
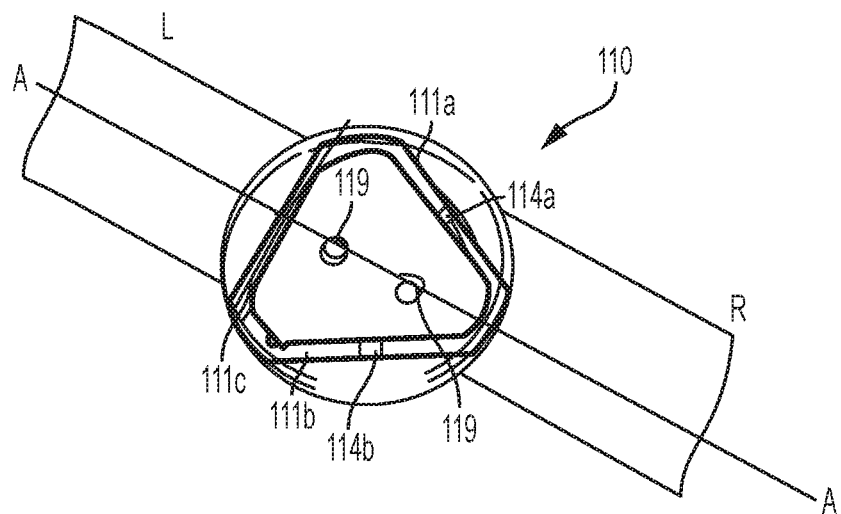
FIG. 5 is a top perspective view of the sheath of FIGS. 1-3 shown anchoring a tendon within a bone hole.

In order to facilitate expansion of the sheath 110, including the cortical retaining flange 113*b*, the sheath 110 can include longitudinal channels 114 (only one channel is shown) formed in opposed sides thereof. The channels 114 having a configuration similar to the channels 14 described above with respect to FIGS. 1-3. The location of the channels 114 is best shown in FIG. 5, which illustrates the three sidewalls (a first sidewall 111*a*, a second sidewall 111*b*, and a third sidewall 111*c*), with channel 114*a* formed at a mid-point of the first sidewall 111*a* and channel 114*b* formed at a mid-point of the second sidewall 111*b*. The sheath 110 of FIGS. 4 and 5 also includes first and second prongs 119, similar to prongs 19 of FIGS. 1-3. In this embodiment, the prongs 119 have a longer length such that the prongs are configured to extend entirely through a tendon. A person skilled in the art will appreciate that the length can vary as desired. As shown in FIG. 5, the prongs are preferably aligned along a longitudinal axis A, with the first sidewall 111*a*, the second sidewall 111*b*, and the channels 119*a* and 119*b* positioned on opposite sides of the axis A. The third sidewall 111*c* extends substantially perpendicular to the axis A. Such a configuration will allow the sheath 110 to separate in a direction substantially perpendicular to the axis A, such that half of the first and second sidewalls 111*a*, 111*b* move toward the right R side of the tendon, and the other half of the first and second sidewalls 111*a*, 111*b*, along with the third sidewall 111*c*, move toward the left L side of the tendon. The sidewalls once separated will thus compress the tendon into the bone, thereby facilitating anchoring of the tendon within the bone hole. The sheath of FIGS. 1-3 can also function in a similar manner. A person skilled in the art will appreciate that the prongs can be oriented in a parallel or a perpendicular orientation in any of the embodiments disclosed herein. For example, in the embodiment of FIG. 5, the prongs can be positioned on opposite sides of the longitudinal axis A.

Figure 6:
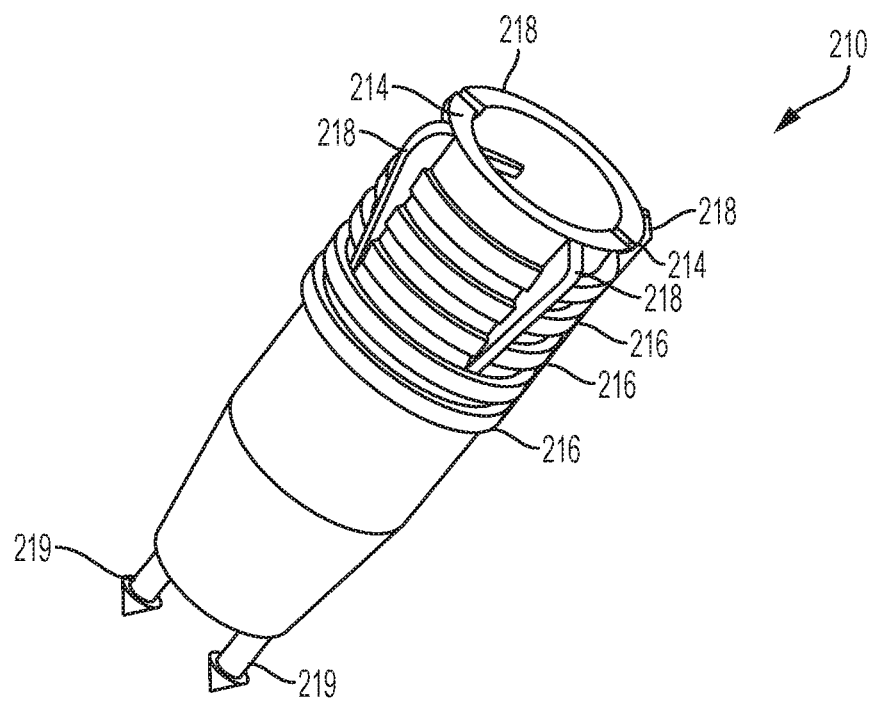
FIG. 6 is a side perspective view of another embodiment of a sheath with a barbed post.

FIG. 6 illustrates another embodiment of a sheath 210. In this embodiment, the sheath 210 has a generally circular cross-sectional geometry, rather than a triangular cross-sectional geometry. The general shape of the body is the same, with the proximal portion being substantially cylindrical with a constant diameter, and the distal portion tapering distally inward. The sheath 210 is otherwise similar to the sheath 10 of FIGS. 1-3, and includes radial ribs 216 and longitudinal ribs 218 along the proximal portion thereof, with the distal portion being surface-feature free. In this embodiment, the sheath 210 has four longitudinal ribs 218 spaced around the perimeter of the sheath 210. The sheath 210 also includes relief channels 214 similar to channels 14 of FIGS. 1-3. In this embodiment, the sheath 210 has two relief channels 214 positioned on opposite sides of the sheath 210 such that the sheath 210 when expanded will separate into two sidewalls, with two of the longitudinal ribs 218 positioned on one of the sidewalls for seating one leg of the tendon therebetween, and the other two longitudinal ribs being positioned on the other sidewall for seating the other leg of the tendon therebetween. The sheath 210 also has first and second prongs 219 that are similar to prongs 19 described above with respect to FIGS. 1-3, however in this embodiment the prongs are barbed such that they are configured to pierce and hold the tendon. The prongs are also oriented to be positioned perpendicular to the longitudinal axis of a tendon, rather than parallel.

Figure 7:
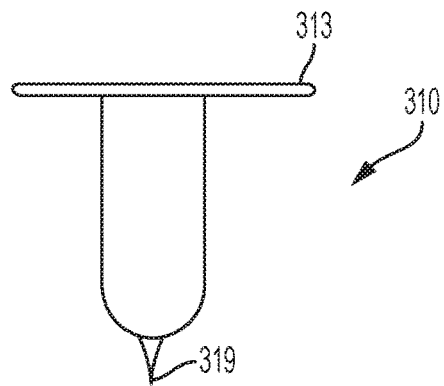
FIG. 7 is a side view of another embodiment of a sheath have a long distal spike feature to engage a tendon.
Figure 8:
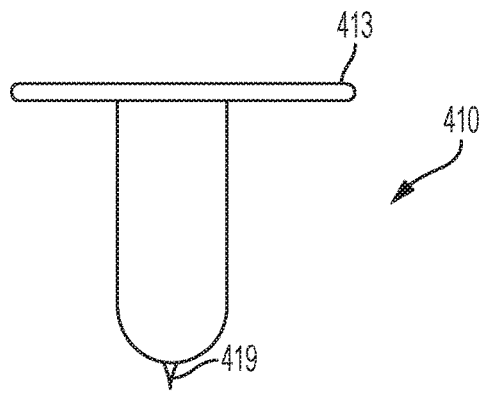
FIG. 8 is a side view of another embodiment of a sheath having a short distal cleat feature.
Figure 9:
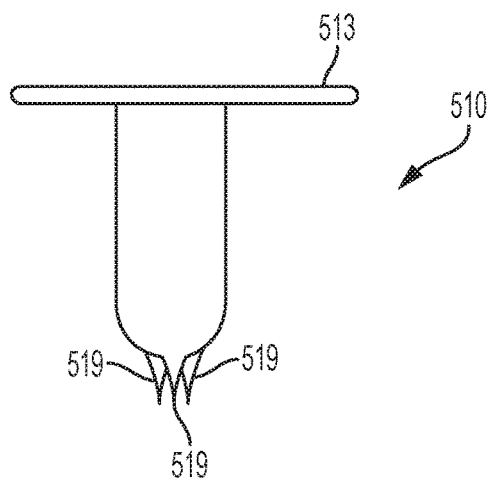
FIG. 9 is a side view of another embodiment of a sheath having a plurality of distal spike features.

As indicated above, the tendon engaging feature on the distal end of the sheath can have a variety of other configurations. FIGS. 7-9 illustrate additional embodiments of sheaths having tendon engaging prongs. In the embodiment of FIG. 7, the sheath 310 has a single prong 319 that is pointed and thus in the form of a spike for penetrating through a tendon, and that has a longer length, e.g., a length that is greater than a thickness of a tendon, so as to allow the prong 319 to extend entirely through the tendon. The single prong 319 is positioned at a mid-point on the distal end of the sheath 310. FIG. 8 illustrates a similar sheath 410 with a single prong 419 in the form of a cleat, however the prong 419 is shortened in length such that the prong 419 only penetrates into and grips the tendon without extending entirely through the tendon. FIG. 9 illustrates a sheath 510 having three prongs 519, in the form of spikes, that extend distally from the distal end of the sheath. The prongs 519 are positioned in a triangular pattern and are closed together so as to allow all three prongs 510 to penetrate into the tendon. The prongs also have a longer length such that they can extend entirely through a tendon. A person skilled in the art will appreciate that the sheath can include any number of prongs having various lengths to inflict a desired amount of trauma on the tendon so as to allow the tendon to be engaged and moved and maintained by the sheath.

The sheaths 310, 410, 510 in FIG. 7-9 each further include a proximal flange 313, 413, 513 extending radially outward from a proximal most end thereof. The proximal flanges can each be configured to compress a tendon against a top outer surface of the bone to help anchor the tendon in position. Each flange 313, 413, 513 can include one or more relief channels or cut-outs formed therein and aligned with one or more relief channels or slots formed in the sheath to allow expansion of the sheath.

Figure 10A:
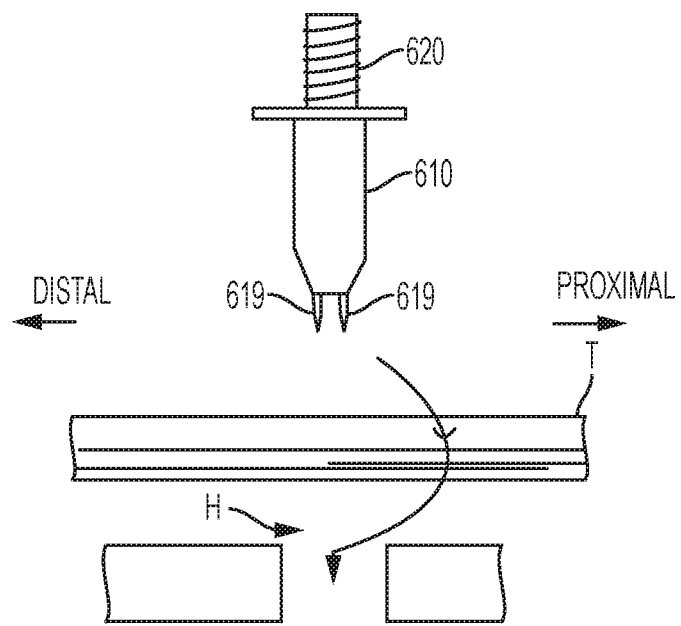
FIG. 10A is a side view of another embodiment of a sheath having two distal spike features, shown about to anchor a tendon within a bone hole and receive an expander to secure it in place.
Figure 10B:
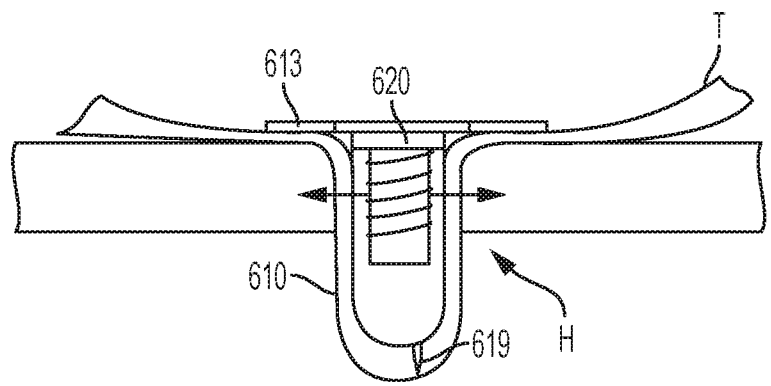
FIG. 10B is a side view of the sheath and tendon of FIG. 10A, shown inserted into the bone hole with the expander inserted therein.
Figure 11:
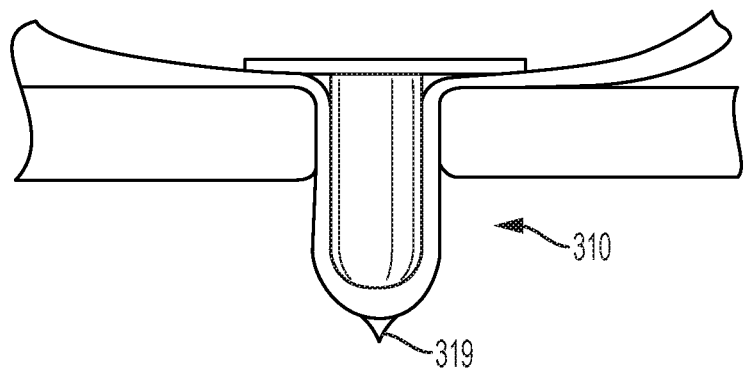
FIG. 11 is a side view of another embodiment of a sheath having a distal barbed post, shown anchoring a tendon within a bone hole.

FIGS. 10A-10B illustrate a method of anchoring a tendon within a bone hole. While the method can be performed using any of the various sheaths and expanders disclosed herein, FIGS. 10A-10B are described in connection with sheath 610 and expander screw 620, which have a configuration similar to the sheath of FIGS. 7-9 and the expander screw of FIG. 1. In this embodiment, the sheath 610 includes a pair of shorter prongs 619, in the form of spikes, positioned in parallel and extending distally from the distal surface of the sheath. FIG. 10A illustrates a tendon T extending across a bone hole H. With the tendon held at a desired tension, the prongs 619 can be used to pierce the tendon at a location proximal to and laterally offset from the bone hole, as indicated by the arrow. The tendon is pierced at a more proximal location so as to account for the depth of the bone hole that the tendon is pushed into (in an effort to restore anatomical tension of the tendon). With the tendon pierced and engaged by the sheath 610, the sheath 610 can be advanced into the bone hole H thereby "dunking" the tendon into the bone hole. As shown in FIG. 10B, when the sheath 610 is fully inserted into the bone hole H, the anti-plunge flange 613 will abut against the top surface of the bone and tendon, thereby compressing the tendon T against the bone. The expander screw 620 can then be advanced into the sheath, e.g., by threading the expander screw 620 into the sheath 610, to cause radial expansion and anchoring of the sheath 610 within the bone hole. As shown in FIG. 10B, the prongs 619 will remain penetrated into the tendon thereby further preventing slippage of the tendon. In this embodiment, the prongs 619 are shortened so that they do not extend entirely through the tendon. FIG. 11 illustrates the sheath 310 of FIG. 7, showing the longer barbed prong 319 penetrating entirely through the tendon.

Figure 10C:
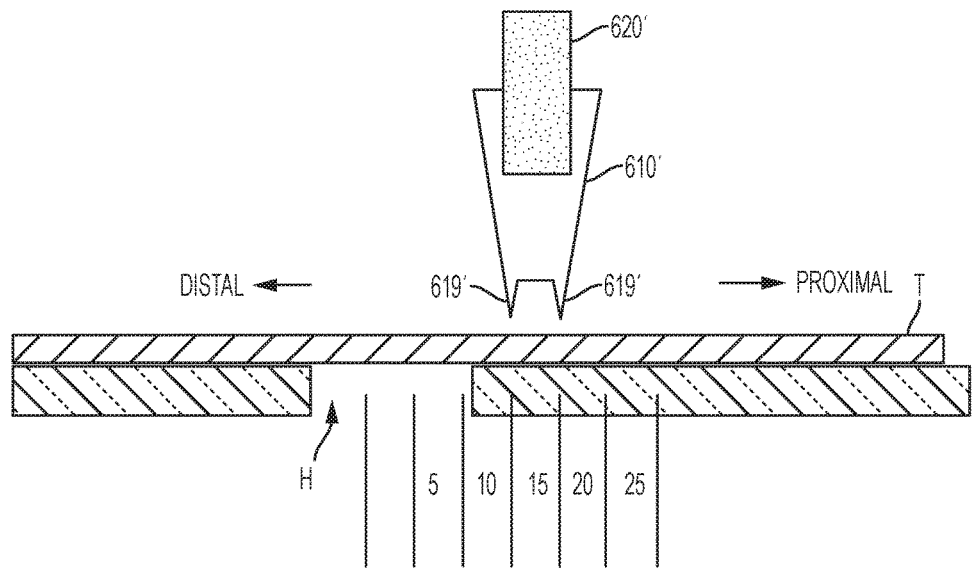
FIG. 10C is a side view of another embodiment of a sheath having a pair of distal spike features shown measuring a distance along a tendon from a bone hole.
Figure 10D:
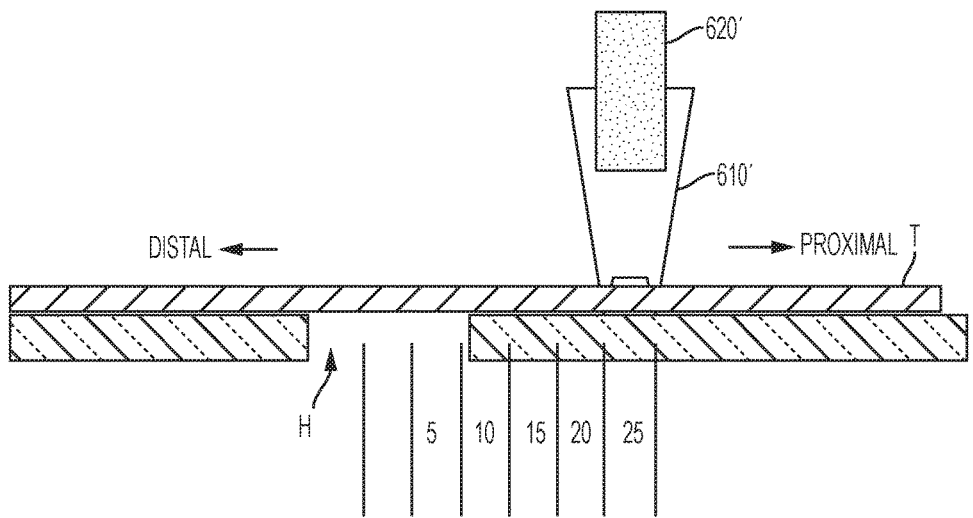
FIG. 10D is a side view of the sheath and tendon of FIG. 10C, showing the sheath engaging the tendon.

FIGS. 10C-10E illustrate another method of anchoring a tendon within a bone hole. When a tendon is positioned at a desired tension across a bone hole and a sheath is used to engage and advance the tendon into the bone hole, the sheath would pull the tendon into the bone hole thereby undesirably altering the tension. In order to allow a tension of the tendon to be maintained, the sheath would need to engage the tendon at a distance from the bone hole. When the tendon T is pierced at a more proximal location, so as to account for a known depth of the bone hole H that the tendon T is pushed into, no additional force is created on the tendon. In one embodiment, the distance can be equal to a depth of the bone hole. By having the amount of tendon pulled into the bone hole equal to a depth of the bone hole, the tension on the tendon can remain unaltered.

FIGS. 10C-10E illustrate a method of using a sheath to measure a distance from a bone hole, thus allowing a user to engage the tendon at a distance from the bone hole that is substantially equal to a depth of the bone hole. While the method can be performed using any of the various sheaths and expanders disclosed herein, FIGS. 10C-10E are described in connection with a sheath 610' and an expander screw 620' that have a configuration similar to the sheath of FIGS. 7-9 and the expander screw of FIG. 1. In this embodiment, the sheath 610' includes a pair of prongs 619' positioned in parallel and extending distally from the distal surface of the sheath. The prongs 619' on the sheath can be a known or fixed distance apart. By way of non-limiting example only, the prongs 619' can be spaced 5 mm apart. FIG. 10C illustrates a tendon T extending across a bone hole H and maintained at a desired tension. With the tendon held at the desired tension, the prongs 619' can be used to measure a distance along the tendon from the bone hole H. The distance is preferably equal to the length of the sheath, however the distance can be modified to increase or decrease a tension applied to the tendon. By way of non-limiting example, for a sheath having a length of 25 mm, the prongs can be used to measure, in 5 mm increments, a distance that is 25 mm from the bone hole. This can be achieved by either positioning or repositioning the prongs in 5 mm increments from the bone hole, or by positioning the prongs on the tendon, and rotating or "walking" the prongs to move the sheath in 5 mm increments away from the bone hole. Once the sheath is positioned at a desired distance, e.g., 25 mm, from the bone hole, the prongs can be engaged into the tendon. As shown in FIG. 10D, the spikes 619' are rotated prior to engaging the tendon to align the spikes perpendicular to the axis of the tendon T. Once the spikes 619' are engaged with the tendon T, the tendon T can be positioned over the bone hole for insertion, as shown in FIG. 10E. The sheath and tendon can then be fully inserted into the bone hole H. In this embodiment, and again referring back to FIG.

10B, the prongs 619' will remain engaged into the tendon thereby further preventing slippage of the tendon.

Figure 12:
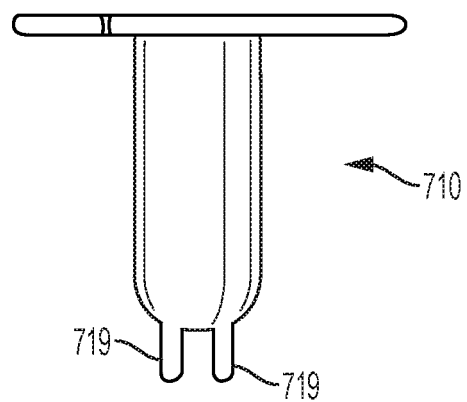
FIG. 12 is a side view of another embodiment of a sheath having two blunted posts, forming a feature disposed on the distal end thereof.

While FIGS. 7-11 illustrate pointed prongs that are configured to penetrate partially or entirely through the tendon, in other embodiments the prong(s) can have a blunt tip configuration so as to poke the tendon without puncturing into the tendon. FIG. 12 illustrates an embodiment of a sheath 710 having prongs 719 that have a rounded tip. In this embodiment, the sheath 710 includes two prongs 719 that are spaced a distance apart that is less than a width of a tendon so as to allow the prongs to poke into the tendon, rather than to straddle the tendon.

Figure 13A:
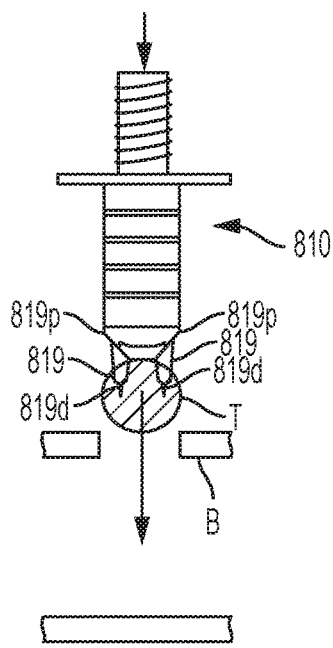
FIG. 13A is a side view of another embodiment of a sheath having flexible distal prongs, shown engaging a tendon about to be inserted into a bone hole and about to receive an expander.
Figure 13B:
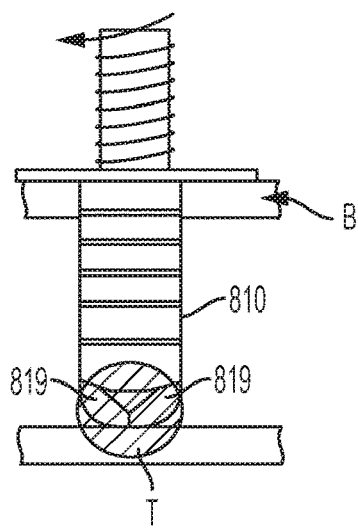
FIG. 13B is a side view of the sheath and tendon of FIG. 13A inserted into the bone hole, showing the flexible prongs closed to pinch and secure the tendon.

In other embodiments, the tendon engaging feature can be movable so as to grasp the tendon. FIGS. 13A-13B illustrate a sheath 810 having a tendon engaging feature in the form of a fork with folding tips 819 extending distally from the distal-most surface of the sheath 810. Each tip has a generally elongate triangular configuration with a pointed distal tip 819*d* for poking or penetrating into a tendon. Depending on the size of the tendon, the tips could alternatively be configured to straddle the tendon. A proximal end 819*p* of each tip can be hingedly coupled to the sheath, e.g., using a pivot joint or by a thinned connection point that allows the material to flex at the joint. In use, the tips 819 of the sheath 810 can be penetrated into a tendon T, as shown in FIG. 13A, and then the sheath 810 and tendon T can be advanced into a bone hole B. The sheath 810 can have a length that causes the tips 819 to contact an opposite surface of the bone, thereby causing the tips to fold inward toward one another and toward the central vertical axis of the sheath, as shown in FIG. 13B. The tips 819 will thus pinch and engage the tendon T, thereby preventing slippage of the tendon. Such a configuration is particularly advantageous with shallow bone holes, wherein the prongs have the capability of collapsing if they "bottom-out" in a shallow hole, thereby allowing the prongs to pinch the tendon and additional secure it in place. An expander screw can then be inserted into the sheath to anchor the sheath and the tendon within the bone hole, as previously described.

Figure 14A:
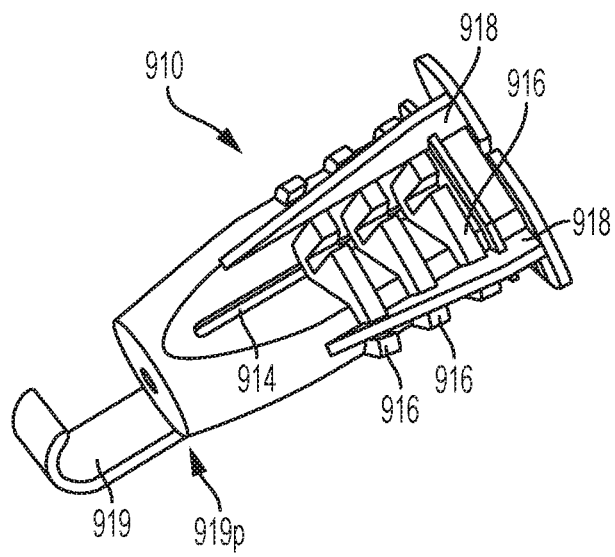
FIG. 14A is a perspective view of another embodiment of a sheath having a distal hook.
Figure 14B:
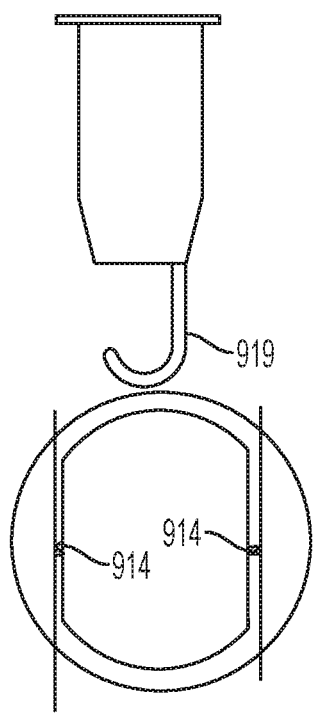
FIG. 14B is a side and a top view of the sheath of FIG. 14A, showing alignment of the sheath with the bone hole.

In another embodiment, the tendon engaging feature can be in the form of a hook, open loop, or closed loop. FIG. 14A illustrates an embodiment of the sheath 910 that is somewhat similar to the sheath of FIGS. 1-6 in that it includes radial ribs 916, longitudinal ribs 918, relief channels 914, an anti-plunge flange 913*a*, and a cortical retaining flange 913*b*. In this embodiment, however, the tendon engaging feature is in the form of a J-shaped hook 919 extending from the distal-facing surface. The hook can be formed from a generally planar elongate rectangular member that is curved at its distal end to create the J-shape. The proximal end 919*p* of the hook 919 is attached to one side of the sheath 910, with the hook extending across the central longitudinal axis. The attachment location of the hook is preferably oriented such that that hook is aligned with the relief channels 914 in the sheath. Such a configuration will allow the tendon, when seated within the hook, to extend along opposed sides of the sheath with the relief channels 914 located between the tendon legs. In an exemplary embodiment, the hook can be oriented as shown in FIG. 14B, which illustrates the hook 919 both before insertion and after insertion into a bone hole. The relief channels 914 can be formed at a location such that they are positioned in-line with the hook. As a result, the sheath will split in half, with one sidewall of the sheath moving toward one leg of the tendon and the other sidewall of the sheath moving toward the other leg of the tendon.

Figure 15A:
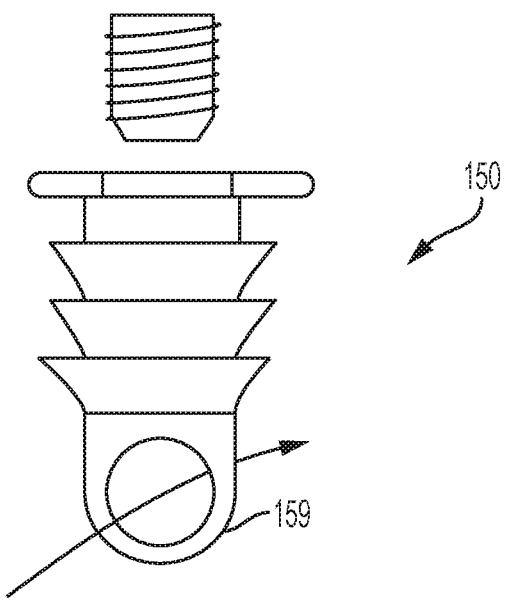
FIG. 15A is a side view of another embodiment of a sheath having a distal ring or hoop for retaining the tendon.
Figure 15B:
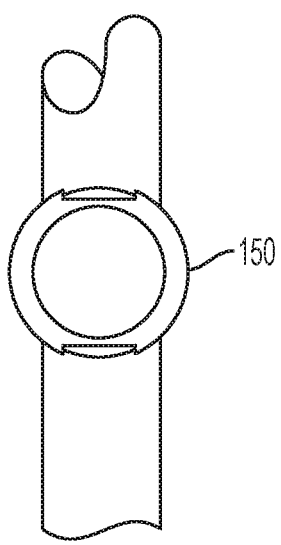
FIG. 15B is a top view of the sheath of FIG. 15A, showing the tendon passing through the ring or hoop.

In another embodiment, as shown in FIG. 15A-15B, the tendon engaging feature on the sheath 150 can be in the form of a fully enclosed hoop or ring 159. The ring 159 can have an outer diameter that matches an outer diameter of the sheath 150 such that the ring 159 extends from both sides of the sheath. This configuration will allow the tendon to be threaded through the ring 159 prior to inserting the sheath into a bone hole. In use, the central axis of the ring 159 is preferably oriented in line with the tendon so as to allow the tendon to extend in a straight configuration around the sheath 150. A person skilled in the art will appreciate that while a circular ring is shown, the hoop or ring can have various shapes, such as oblong or elliptical, square, etc.

Figure 16:
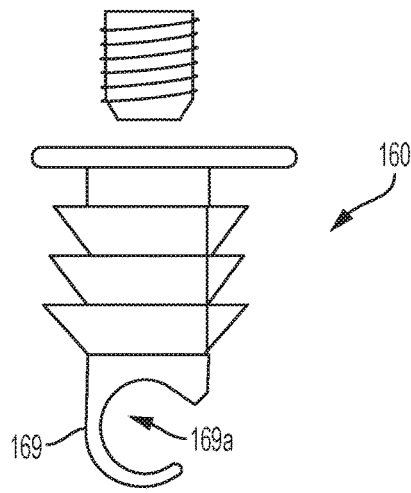
FIG. 16 is a side view of another embodiment of a sheath having a distal hook for engaging the tendon.
Figure 17:
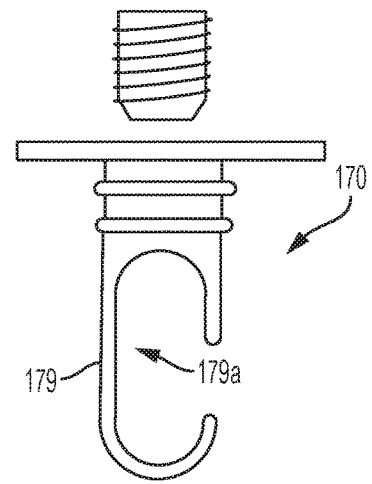
FIG. 17 is side view of another embodiment of a sheath having a distal hook for engaging and retaining the tendon.
Figure 18:
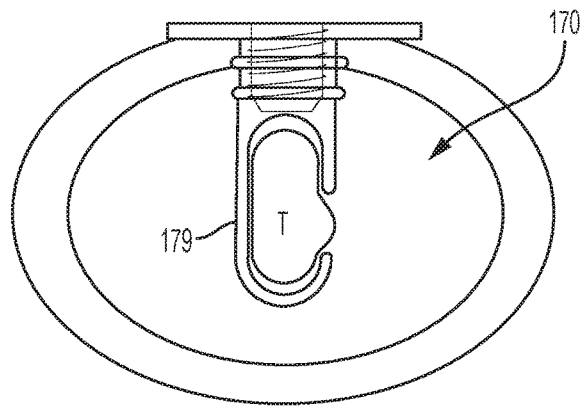
FIG. 18 is a side view of the sheath of FIG. 17 and a cross-sectional view of bone, showing the sheath implanted in bone.

In another embodiment, shown in FIG. 16, the sheath 160 can include a split ring or semi-circular ring that has a cut-out or opening 169*a* in a side thereof so as to allow the tendon to be passed into the ring from the side, rather than threaded therethrough. In other embodiments, the length of the ring can vary such that the ring has an oblong configuration. FIG. 17 illustrates a sheath 170 having an oblong ring 179 with an opening 179*a* in a side thereof, similar to a carabiner. FIG. 18 illustrates the sheath 170 of FIG. 17 implanted in bone. As shown, the oblong shape of the ring 179 allows the entire tendon to be received therein. In the embodiment of FIG. 18, the sheath body has a relatively short configuration, with a length that is less than a length of the ring 179. Such a configuration allows for a larger volume of tendon to be captured in the ring 179.

Figure 19A:
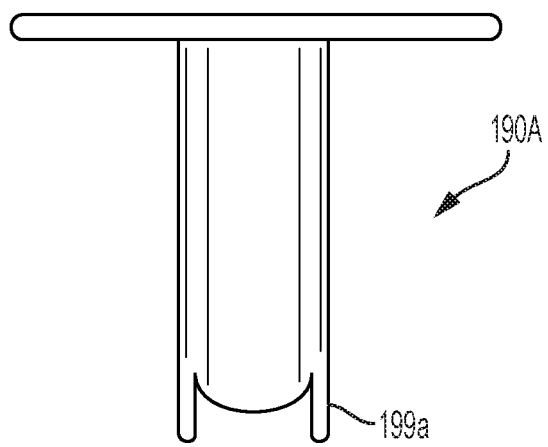
FIG. 19A is a side view of another embodiment of a sheath having a pair of short, wide set blunted posts forming forks extending distally therefrom.
Figure 19B:
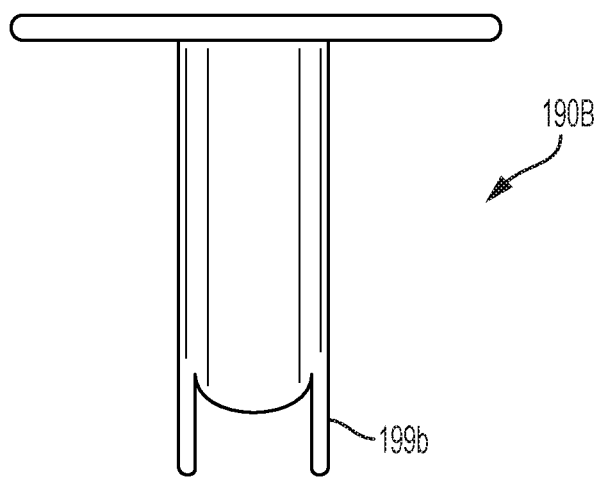
FIG. 19B is a side view of another embodiment of a sheath having a pair of long, wide set blunted posts forming forks extending distally therefrom.

While each of the aforementioned embodiments include sheaths having tendon engaging features that poke, penetrate, or otherwise grasp or engage a tendon, in other embodiments the tendon engaging features can be configured to straddle a tendon, e.g., receive a tendon therebetween. FIGS. 19A-19B illustrate one such embodiment of a sheath 190A having a pair of distal blunted forked tips 199*a* that extend substantially parallel to one another from opposed sidewalls of the sheath. Since the tips extend from the outermost sidewalls of the sheath 190A, the tips 199*a* are configured to receive a tendon therebetween, rather than to penetrate into a tendon. The length of the fork tips can also vary. FIG. 19A represents short tips 199A, while FIG. 19B illustrates an embodiment of a sheath 190B having long tips 199*b* with a larger tendon seating recess formed therebetween. The longer tips can also be particularly suitable for measuring a size of a tendon.

Figure 20A:
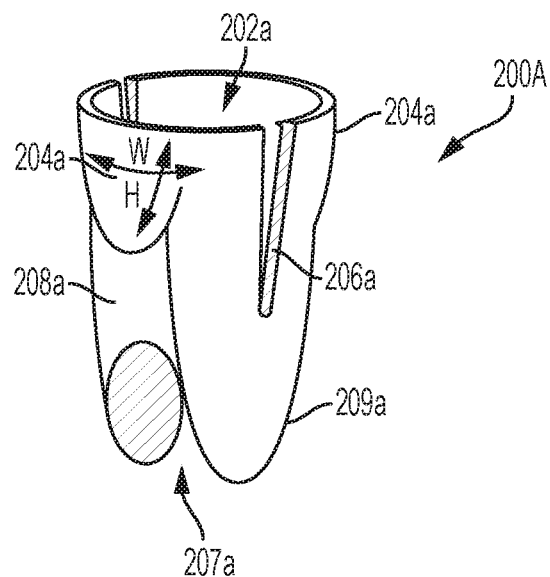
FIG. 20A is a side perspective view of another embodiment of a sheath having opposed expansion slots and a u-shaped distal channel for engaging a tendon.
Figure 20B:
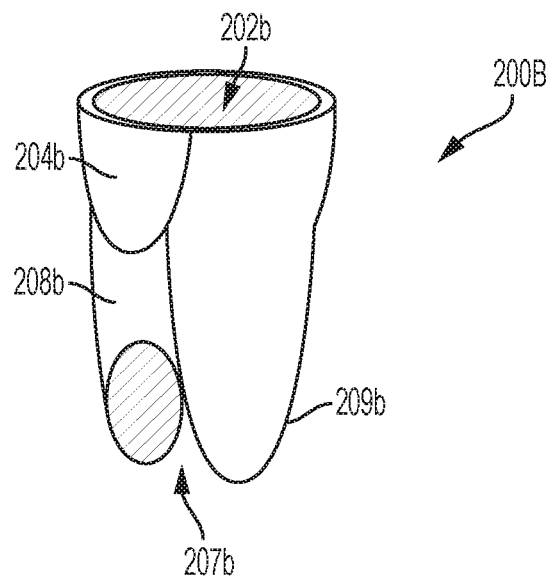
FIG. 20B is side perspective of another embodiment of a sheath.

FIG. 20A illustrates another embodiment of a sheath As shown in FIG. 20A, the sheath 200A has a generally elongate cylindrical configuration with an inner lumen 202*a* extending from an open proximal end and terminating proximal to a closed distal end. The proximal end can include a funnel shaped bump-out 204*a* on opposed sides thereof so as to create an elongate opening. The funnel bump-outs 204*a* can thus serve as a lead-in for the expander screw. The width W of each funnel bump-out can vary, and the bump-outs can extend fully or partially around an entire half of the sheath circumference. The height H of each bump-out 204*a* can also vary, but preferably each bump-out 204*a* only extends along a proximal portion of the sheath 200A. When the funnel shape is expanded it can press the tendon against the bone. As further shown in FIG. 20A, the sheath can also include a concave outer sidewall 208*a* on opposed sides thereof (only one sidewall is shown) at a location aligned with and extending distally from the bump-outs 204*a*. The remaining sidewalls connecting the opposed concave sidewalls 208*a* can have a convex configuration. The tendon can be configured to extend along the concave sidewalls 208*a* and along the funnel bump-outs 204*a*. The convex sidewalls can include cut-outs or slots 206a, as shown, for allowing the sheath 200A to expand when an expander is inserted therein. The elongate slots 206a can extend from the proximal end and can terminate proximal to the distal end. As shown in FIG. 20A, the slots 206a terminate at a mid-portion of the sheath 200A. Alternatively, as shown in FIG. 20B, the sheath 200B can include relief channels (not shown) formed on an inner and/or outer surface thereof that are configured to break during expansion of the sheath. FIG. 20B is otherwise identical to FIG. 20A, and thus like reference numbers are used to refer to like parts.

Continuing to refer to FIG. 20A, the distal end of the sheath can include opposed extension tabs 209a extending from the concave sides thereof, i.e., the sides having the slots 206a formed thereon. The extension tabs 209a can each have a generally rounded distal end and they can define a U-shaped recess 207a therebetween for seating a tendon. The length of the tabs and the depth of the recess can vary as desired depending on the size of the tendon to be received therebetween.

Figure 21:
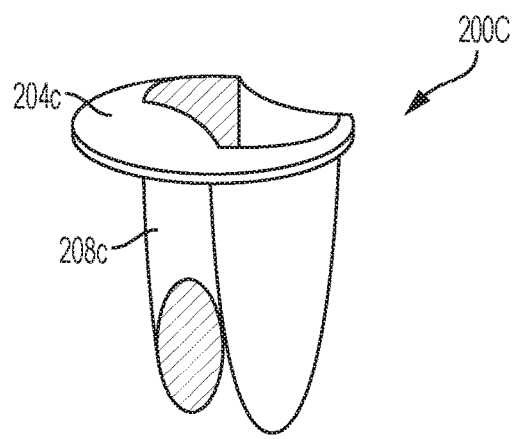
FIG. 21 is side perspective of another embodiment of a sheath with a proximal retention feature.
Figures 22A, 22B:
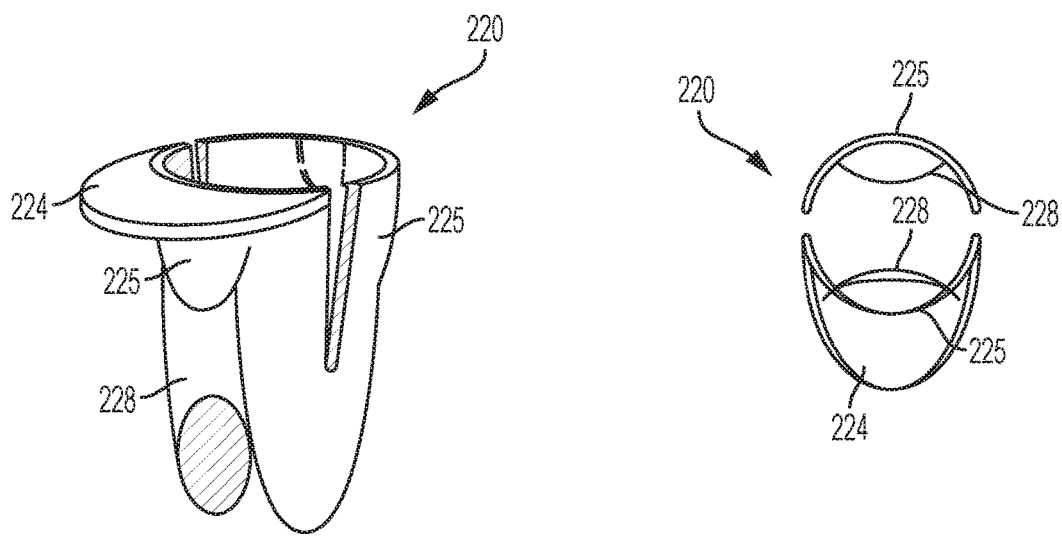
FIG. 22A is side perspective of another embodiment of a sheath with a proximal retention feature and a pair of opposed slots.
FIG. 22B is a top view of the sheath of FIG. 22A.

FIG. 21 illustrates another embodiment of a sheath 200C that is similar to sheath 200A of FIG. 20A, but in this embodiment rather than having funnel bump-outs the sheath includes a proximal tab or flange 204c extending radially outward from one side thereof. In particular, the flange 204c has a generally semi-circular configuration and is coupled to and extends outward from a proximal-most end of one of the concave sidewalls 208c. In use, the flange 204c will abut against an outer surface of the bone, thereby limiting the insertion depth of the sheath 200C into the bone. The flange 204c will also compress the tendon against the bone surface, aiding in anchoring of the tendon. FIG. 22A illustrates yet another embodiment of a sheath 220 having both a flange 224 and opposed funnel bump-outs 225, with one bump-out 225 positioned just distal of the flange 224 such that the flange 224 extends radially outward from a proximal surface of the funnel bump-out 225. FIG. 22B illustrates a top view of the sheath 220, showing the flange 224 extending radially outward from the funnel bump-out 225, and showing the distally-located concave sidewall 228. The opposite side of the sheath 220 similarly includes a funnel bump-out 225 and a concave sidewall 228. In use, the flange 224 will compress the tendon against the bone surface, the bump-outs 225 will compress both legs of the tendon against the sidewalls of the bone hole.

Figure 23A:
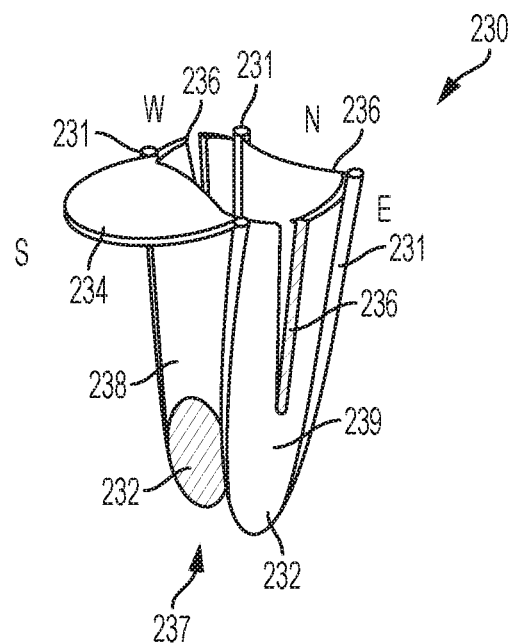
FIG. 23A is a side perspective view of another embodiment of a sheath having a concave sidewalls.
Figure 23B:
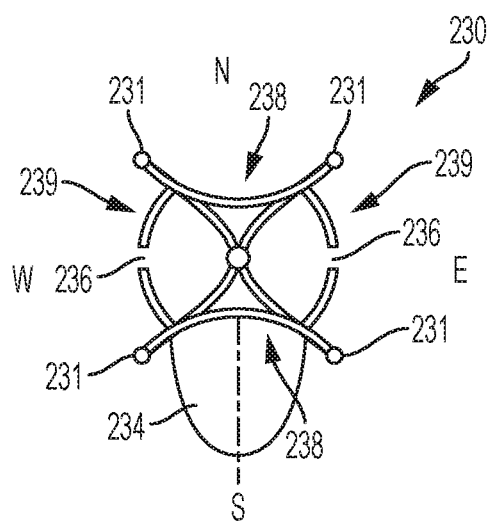
FIG. 23B is a top view of the sheath of FIG. 23A.

FIGS. 23A-23B illustrate another embodiment of a sheath 230 that is similar to sheath 200C of FIG. 21, but that includes sidewall slots 236 for allowing the sheath to expand. In particular, the sheath 230 includes opposed concave sidewalls 238 that curve radially inward and opposed convex sidewalls 209 extending between the concave sidewalls 238 and that have the elongated slots 236 formed therein. The concave sidewalls 238 are each configured to seat a leg of the tendon, with the tendon extending through the tendon seating recess 237 formed between the distal tips 232. In this embodiment, the sheath 230 further includes a roll 231 extending longitudinal along each corner connecting the sidewalls 238, 239. In other words the sheath 230 has four rolls, one at each corner. Each roll can be formed by a portion of each sidewall being folded to create a hollow channel therebetween. Such a configuration can allow the roll to expand and the sidewalls to move away from one another when an expander is inserted into the sheath. The roll thus functions similar to a hinge, allowing the sidewalls to move away from one another without breaking apart. The sheath can further include a proximal flange 234 extending radially outward from one of the concave sidewalls 238. The flange can overly the tendon entering from the side that is attached to the muscle, labeled as south S in the figure. The proximal flange 288 sits on the bone surface and presses the tendon downward and can also serve as an anti-plunge feature. As shown in the overhead view of sheath 230 in FIG. 23B, the east E and west W sidewalls 239 can be outwardly bowing and can include the elongate slots 236. The north N and south S facing sidewalls 238 can be contoured to bow inwards. When the tendon is coupled to the sheath 230 it can extend under the proximal flange 234 and extend along the south facing sidewall 238, around the distal end between the fork tips 232, and upward along the north facing sidewall 238.

Figure 24A:
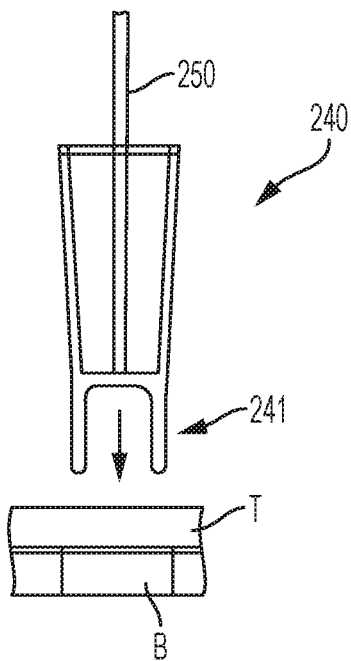
FIG. 24A is a side partially transparent view of a sheath coupled to a guidewire, showing the sheath about to insert a tendon into a bone hole.
Figure 24B:
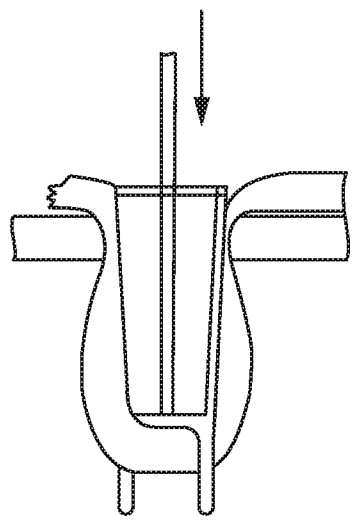
FIG. 24B is a side partially transparent perspective view of the sheath, tendon, and guidewire of FIG. 24A disposed in the bone hole.
Figure 24C:
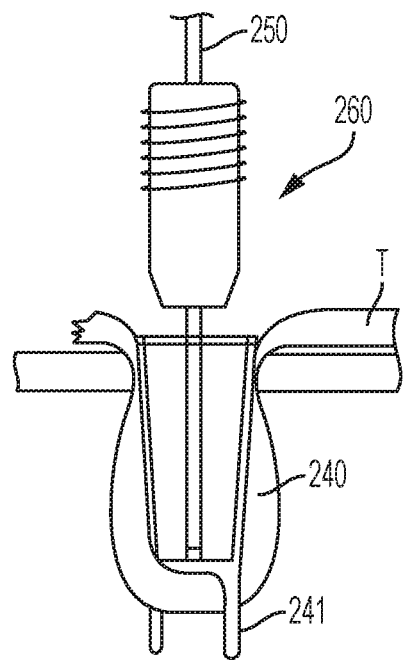
FIG. 24C is a side perspective view of the sheath, tendon, and guidewire of FIG. 24B, showing an expander about to be inserted into the sheath over the guidewire.
Figure 24D:
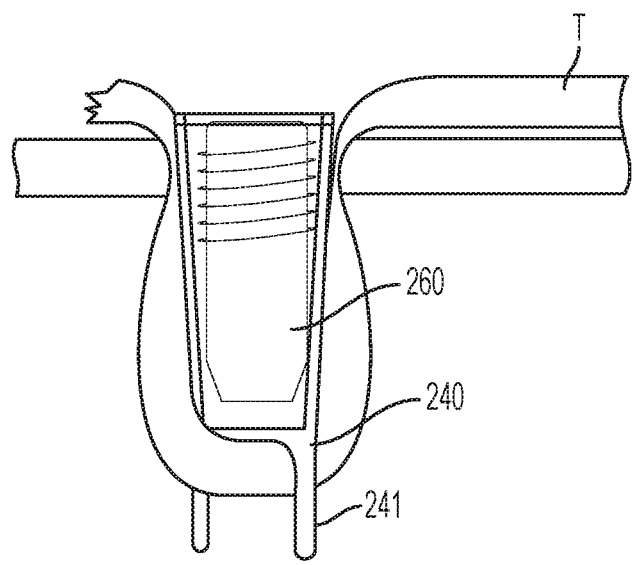
FIG. 24D is a side perspective view of the sheath, tendon and expander of FIG. 24C with the guidewire removed therefrom.

FIGS. 24A-24D illustrate a method of anchoring a tendon to bone using a sheath having a fork tip that is configured to straddle the tendon. A person skilled in the art will appreciate that the method can be used in connection with any of the sheaths shown in FIGS. 19A-23B. By way of non-limiting example, a sheath 240 is shown having fork tips 241 at the distal end thereof. The sheath 240 is also shown having a threaded bore formed therein and threadably mated to a threaded tip on a guidewire 250. One exemplary method for utilizing the biceps tenodesis anchor and delivery tools to perform a biceps tenodesis surgery can include preparing the tendon and measuring the tendon. For example, as shown in FIG. 24A, the sheath 240 can be manipulated to position the tendon between the fork tips 241. Different sized sheaths having fork tips with different spacing can be used to assess the size of the tendon. Once the appropriately sized sheath 240 is selected, the fork tips 241 can be positioned around the tendon T, and the sheath 240 can then be inserted into the bone hole B pushing the tendon into the bone hole, as shown in FIG. 24B. The tendon T will extend along opposed sides of the sheath. While not shown, an inserted tool can be coupled to the guidewire and it can be used to facilitate insertion of the sheath and tendon into a bone hole. The inserter tool can be disengaged from the guidewire 250 so that the guidewire 250 remains coupled to the sheath 240 after insertion into the bone hole B. As shown in FIG. 24C, an expander 260 can be advanced over the guidewire 250 and inserted into the sheath 700. While not shown, a driver tool can be coupled to the expander 260 and used to advance the expander along the guidewire and to drive the expander into the sheath. The driver tool can be removed and then the guidewire can be disengaged from the anchor assembly (not shown). As shown in FIG. 24D, the anchor assembly including the sheath 240 and expander 260 remain within the bone hole B with the tendon T extending therearound and positioned between the fork tips 241 at the distal tip of the sheath 700.

A person skilled in the art will appreciate that in any of the embodiments disclosed herein, the prongs can be malleable to allow a surgeon to bend and manipulate the prongs into a desired configuration to facilitate insertion of a tendon into a bone hole.

Figure 25A:
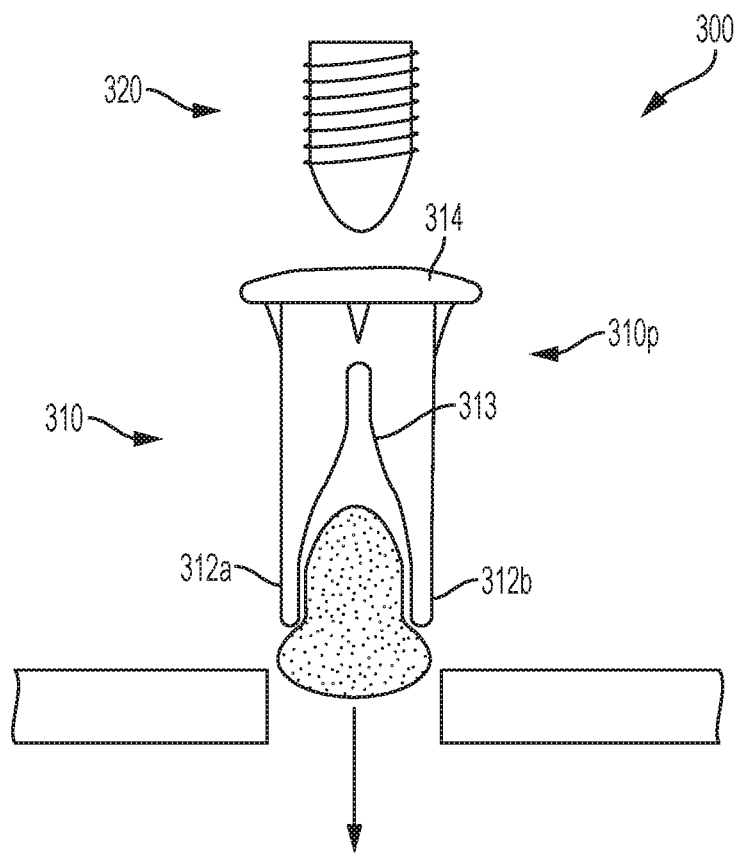
FIG. 25A is a side view of another embodiment of a sheath having an expandable distal end, showing the sheath positioned around a tendon for inserting the tendon into bone, and showing an expander to be received in the sheath.
Figure 25B:
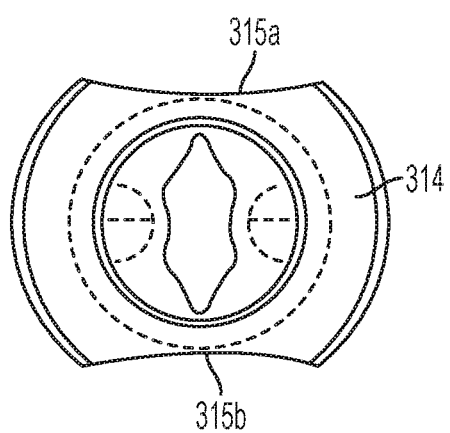
FIG. 25B is a top view of the sheath of FIG. 25A.
Figure 25C:
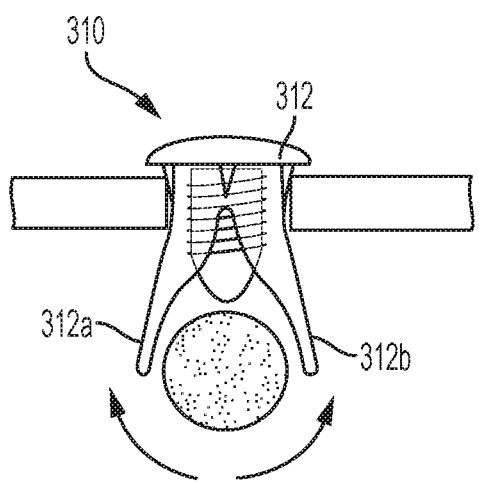
FIG. 25C is a side view of the sheath and expander of FIG. 25A, showing the sheath implanted in bone and expanded for receiving the tendon and anchoring the sheath within the bone.
Figure 25D:
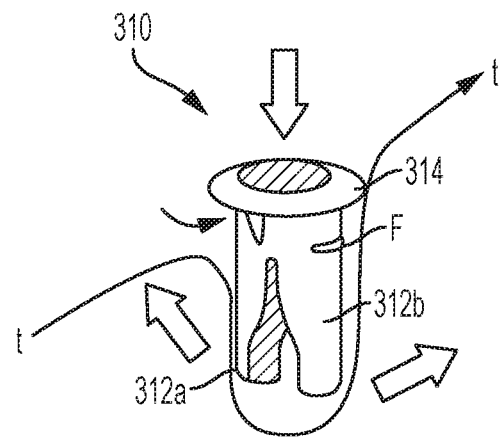
FIG. 25D is a perspective view of the sheath of FIG. 25A.
Figure 25E:
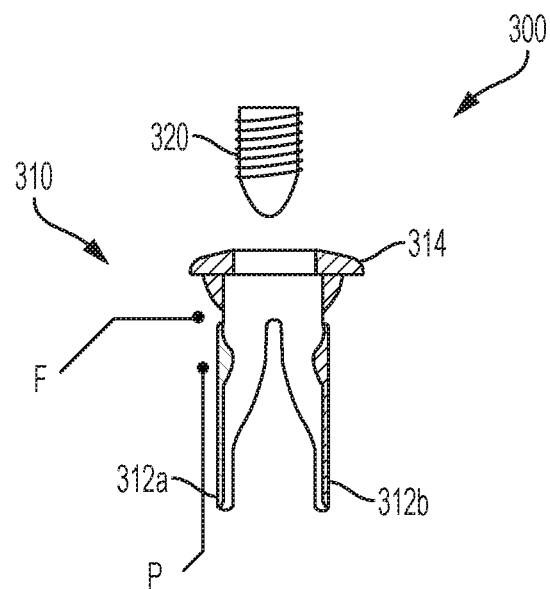
FIG. 25E is a cross-sectional view of the sheath and sheath expander of FIG. 25A.

FIGS. 25A-25E illustrate yet another embodiment of an anchor assembly 300 for anchoring a tendon in bone. In this embodiment, the sheath 310 is split at the distal end 310d such that it is generally cylindrical at the proximal end 310p and along a proximal portion thereof, and two legs 312a, 312b extend distally therefrom. The legs 312a, 312b can be separated by opposed slots (only one slot 313 is shown) formed in the sheath and extending from the distal end 310d and terminating distal to the proximal end 310p. In the illustrated embodiment, the slots are narrower along the proximal portion and wider along the distal portion. The wider distal portion of the slots can seat and engage a tendon therebetween, as shown in FIG. 25C. The tendon can extend in the direction t shown in FIG. 25D. The legs 312*a*, 312*b* can be flexible and can expand radially outward to anchor the sheath 310 within the bone hole. As shown in FIGS. 25D and 25E, the sidewalls can include a relief cut F formed thereon to create a flex point for allowing the legs to pivot outward at relief cut F, as the expander (320) advances past the increased wall thickness (bump, internal mass, rib, etc.)—point P. The relief cut F can be formed at a location just distal to the proximal end 310*p* such that the pivot point P is within or beneath the cortical bone. The relief cut F can be in the form of a slot extending partially or fully through the sidewall of the anchor, and preferably extending at least partially radially around the sidewall so as to allow pivotal movement of the legs 312*a*, 312*b*. The legs 312*a*, 312*b* can have a length such that, when the sheath 310 is implanted in bone, the legs 312*a*, 312*b* extend beneath a surface of the cortical bone and expand radially outward beyond the size of the bone hole to thereby retain the sheath within the bone hole. As further shown in FIGS. 25A-25E, the sheath 310 can optionally include a head or flange 314 formed on the proximal end that abuts against the bone surface to limit an insertion depth of the sheath into bone. The flange 324 can include relief cut-outs 315*a*, 315*b* formed in opposed sides thereof for seating the tendon, as shown in FIG. 25B. The anchor assembly 300 can further include an expander 320 that is configured to be received within an inner lumen extending through the sheath. The expander 320 can be a threaded screw that threadably mates with threads formed on an internal surface of the sheath 310, or in other embodiments the expander 320 can be non-threaded or only partially threaded. Insertion of the expander into the sheath can cause the legs to expand radially outward. A person skilled in the art will appreciate that a variety of other techniques can be used to cause expansion of the distal end of the sheath.

A person skilled in the art will appreciate that the biceps tenodesis methods and devices disclosed herein can be used in a variety of surgical procedures to trauma or damage to a tendon being attached to a bone via a bone hole. The present invention also has application in conventional joint repair surgeries.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An anchor assembly for anchoring a tendon to bone, comprising:
   a substantially cylindrical sheath having bone-engaging surface features formed on an external surface thereof, and having an inner lumen formed therein and extending from an open proximal end to a closed distal end, the closed distal end having a threaded bore configured to receive a threaded tip of a guidewire therein, and the closed distal end having two tendon anchoring features defining a recess therebetween for seating a tendon; and
   an expander having an elongate cylindrical configuration and being sized and shaped to be received within the inner lumen of the sheath, the expander having a lumen extending therethrough for receiving the guidewire.

2. The anchor assembly of claim 1, wherein the two tendon anchoring features comprise two prongs extending distally from a distal-facing surface of the sheath.

3. The anchor assembly of claim 1, wherein the tendon anchoring features comprise first and second barbed prongs extending parallel to one another.

4. The anchor assembly of claim 1, wherein the two tendon anchoring features each comprise a prong having a distal pointed tip configured to penetrate through tissue.

5. The anchor assembly of claim 1, wherein the sheath includes at least one rib formed on the external surface thereof and extending longitudinally in a proximal-distal direction.

6. The anchor assembly of claim 1, wherein the expander includes a flange extending radially outward from a proximal end thereof.

7. An anchor assembly for anchoring a tendon to bone, comprising:
   a sheath having a body having only two sidewalls extending proximally therefrom and forming first and second halves of the body, the sidewalls defining an inner lumen therebetween, and the sidewalls having threads formed on an internal surface thereof, the sheath having an internal distal threaded bore configured to mate with a threaded tip of a guidewire and the sheath having first and second tendon engaging features extending distally from a distal-most surface thereof, the tendon engaging features defining a graft seating recess therebetween; and
   a threaded expander configured to be received between the two sidewalls and to threadably mate with the threads formed on the internal surface of the sidewalls;
   wherein the sheath and the threaded expander are configured such that, when the expander is fully threaded into the sheath, the sheath expands radially outward to retain a tendon within a bone hole.

8. The anchor assembly of claim 7, wherein the sidewalls include radial ribs and longitudinal ribs formed on an external surface thereof, the longitudinal ribs extending in a proximal-distal direction transverse to the radial ribs.

9. The anchor assembly of claim 7, wherein an outer diameter of the sheath is tapered along a distal portion of the sheath.

10. The anchor assembly of claim 8, wherein the radial ribs are formed on a proximal portion of the sheath and a distal portion of the sheath is rib-free.

11. An anchor assembly for anchoring a tendon to bone, comprising:
    a substantially cylindrical sheath having bone-engaging surface features formed on an external surface thereof, and having an inner lumen formed therein and extending from an open proximal end to a closed distal end, the closed distal end having a threaded bore configured to receive a threaded tip of a guidewire therein and a fork-shaped distal end with first and second prongs configured to seat a tendon therebetween; and
    an expander having an elongate cylindrical configuration and being sized and shaped to be received within the inner lumen of the sheath, the expander having a lumen extending therethrough for receiving the guidewire.

* * * * *